United States Patent
Jackson (12)

(10) Patent No.: US 7,833,250 B2
(45) Date of Patent: *Nov. 16, 2010

(54) POLYAXIAL BONE SCREW WITH HELICALLY WOUND CAPTURE CONNECTION

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 1412 days.

This patent is subject to a terminal disclaimer.

(21) Appl. No.: 10/986,377

(22) Filed: Nov. 10, 2004

(65) Prior Publication Data

US 2006/0100622 A1   May 11, 2006

(51) Int. Cl.
*A61B 17/70* (2006.01)

(52) U.S. Cl. ..................................... 606/270

(58) Field of Classification Search .............. 606/246, 606/250–253, 265–269, 270–275
See application file for complete search history.

(56) References Cited

U.S. PATENT DOCUMENTS

| | | | |
|---|---|---|---|
| 5,261,912 A | 11/1993 | Frigg | |
| 5,312,404 A | 5/1994 | Asher et al. | |
| 5,360,431 A | 11/1994 | Puno et al. | |
| 5,429,639 A | 7/1995 | Judet | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,601,553 A | 2/1997 | Trebing et al. | |
| 5,613,968 A * | 3/1997 | Lin ............................ | 606/320 |
| 5,669,911 A | 9/1997 | Errico et al. | |
| 5,672,176 A | 9/1997 | Biedermann et al. | |

(Continued)

FOREIGN PATENT DOCUMENTS

DE      9202745.8      4/1992

(Continued)

OTHER PUBLICATIONS

*EBI Omega 21* Brochure, EBI Spine Systems, pub. 1999.

(Continued)

*Primary Examiner*—Anu Ramana
(74) *Attorney, Agent, or Firm*—John C. McMahon

(57) ABSTRACT

A polyaxial bone screw assembly includes a threaded shank body having an upper capture structure, a head and a closed retainer ring. The external capture structure surface and retainer ring internal bore surface are both threaded for rotatable attachment within a cavity of the head. The head has a U-shaped cradle defining a channel for receiving a spinal fixation rod. The head channel communicates with the cavity and further with a restrictive opening that allows for loading the capture structure into the head but prevents passage of the closed retainer ring out of the head. The retainer ring has an external substantially spherical surface that mates with an internal surface of the head, providing a ball joint, enabling the head to be disposed at an angle relative to the shank body. The threaded capture structure or the closed retainer structure includes a tool engagement formation and gripping surfaces for non-slip engagement by a tool for driving the shank body into bone.

41 Claims, 9 Drawing Sheets

U.S. PATENT DOCUMENTS

| | | | |
|---|---|---|---|
| 5,690,630 | A | 11/1997 | Errico et al. |
| 5,725,528 | A | 3/1998 | Errico et al. |
| 5,728,097 | A * | 3/1998 | Mathews .................. 606/279 |
| 5,728,098 | A | 3/1998 | Sherman et al. |
| 5,733,286 | A | 3/1998 | Errico et al. |
| 5,782,833 | A | 7/1998 | Haider |
| 5,797,911 | A | 8/1998 | Sherman et al. |
| 5,800,435 | A | 9/1998 | Errico et al. |
| 5,817,094 | A | 10/1998 | Errico et al. |
| 5,879,350 | A | 3/1999 | Sherman et al. |
| 5,885,286 | A | 3/1999 | Sherman et al. |
| 5,891,145 | A | 4/1999 | Morrison et al. |
| 5,964,760 | A | 10/1999 | Richelsoph |
| 6,010,503 | A | 1/2000 | Richelsoph et al. |
| 6,019,759 | A | 2/2000 | Rogozinski |
| 6,053,917 | A | 4/2000 | Sherman et al. |
| 6,063,090 | A | 5/2000 | Schlapfer |
| 6,074,391 | A | 6/2000 | Metz-Stavenhagen et al. |
| 6,077,262 | A | 6/2000 | Schlapfer et al. |
| 6,090,110 | A | 7/2000 | Metz-Stavenhagen |
| 6,090,111 | A | 7/2000 | Nichols |
| 6,132,432 | A | 10/2000 | Richelsoph |
| 6,146,383 | A | 11/2000 | Studer et al. |
| 6,187,005 | B1 | 2/2001 | Brace et al. |
| RE37,161 | E | 5/2001 | Michelson et al. |
| 6,224,596 | B1 | 5/2001 | Jackson |
| 6,248,105 | B1 | 6/2001 | Schlapfer et al. |
| 6,254,602 | B1 | 7/2001 | Justis |
| 6,273,888 | B1 | 8/2001 | Justis |
| 6,280,442 | B1 | 8/2001 | Barker et al. |
| 6,287,308 | B1 | 9/2001 | Betz et al. |
| 6,287,311 | B1 | 9/2001 | Sherman et al. |
| 6,302,888 | B1 | 10/2001 | Mellinger et al. |
| 6,368,321 | B1 | 4/2002 | Jackson |
| 6,432,109 | B1 * | 8/2002 | Letendart et al. ............ 606/264 |
| 6,471,705 | B1 | 10/2002 | Biedermann et al. |
| 6,485,494 | B1 | 11/2002 | Haider |
| 6,488,681 | B2 | 12/2002 | Martin et al. |
| 6,554,834 | B1 | 4/2003 | Crozet et al. |
| 6,565,565 | B1 | 5/2003 | Yuan et al. |
| 6,565,567 | B1 | 5/2003 | Haider |
| 6,641,593 | B1 | 11/2003 | Schaller et al. |
| 6,695,843 | B2 | 2/2004 | Biedermann et al. |
| 6,716,214 | B1 | 4/2004 | Jackson |
| 6,835,196 | B2 | 12/2004 | Biedermann et al. |
| 2001/0001119 | A1 | 5/2001 | Lombardo |
| 2002/0143341 | A1 | 10/2002 | Biedermann et al. |
| 2004/0153068 | A1 | 8/2004 | Janowski et al. |
| 2004/0162560 | A1 | 8/2004 | Raynor et al. |
| 2005/0154390 | A1 | 7/2005 | Biedermann et al. |
| 2005/0192571 | A1 | 9/2005 | Abdelgany |
| 2005/0203517 | A1 | 9/2005 | Jahng et al. |
| 2005/0203519 | A1 | 9/2005 | Harms et al. |

FOREIGN PATENT DOCUMENTS

| | | |
|---|---|---|
| DE | 19507141 | 9/1996 |
| EP | 1121902 | 8/2001 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System Brochure*, Surgical Dynamics, pub. 1998-99.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.

* cited by examiner

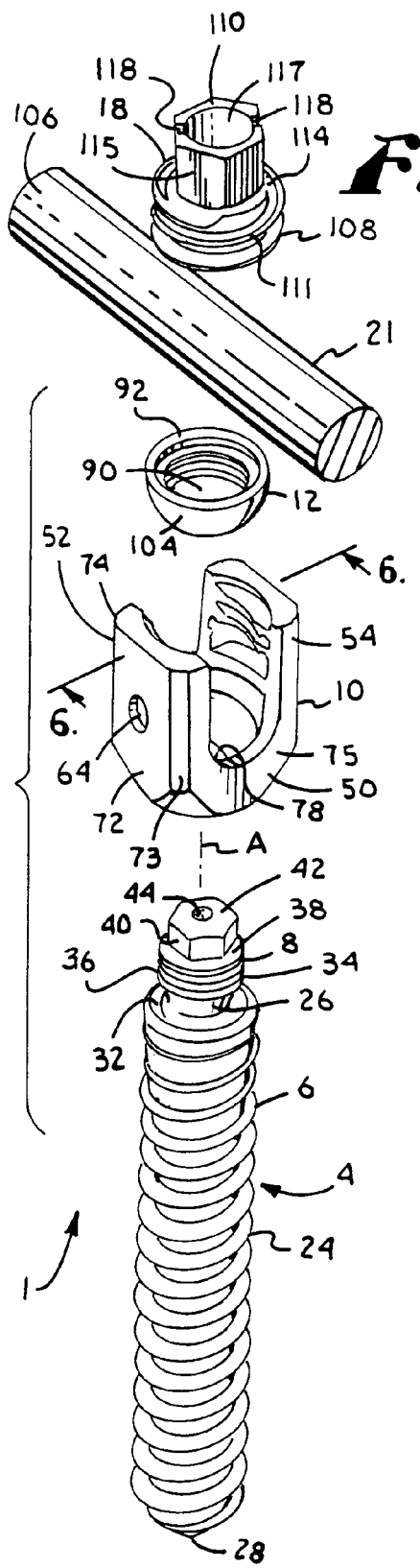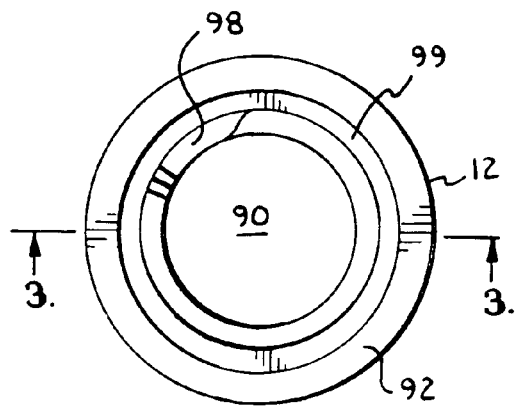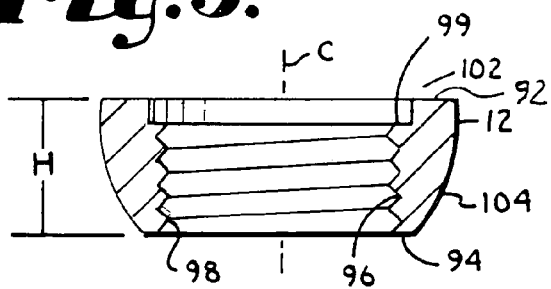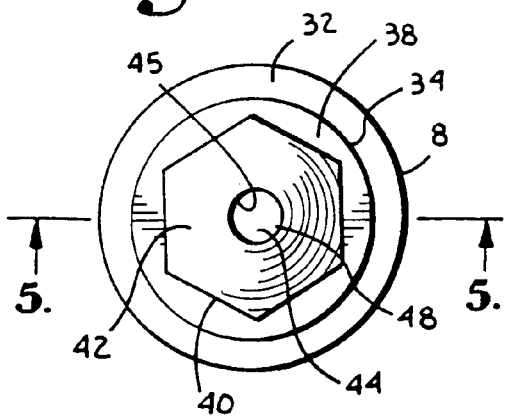

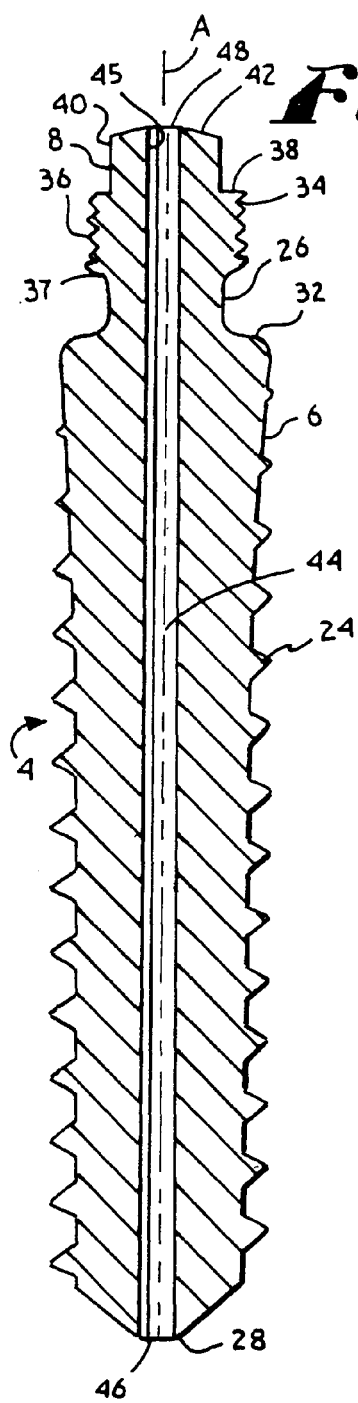
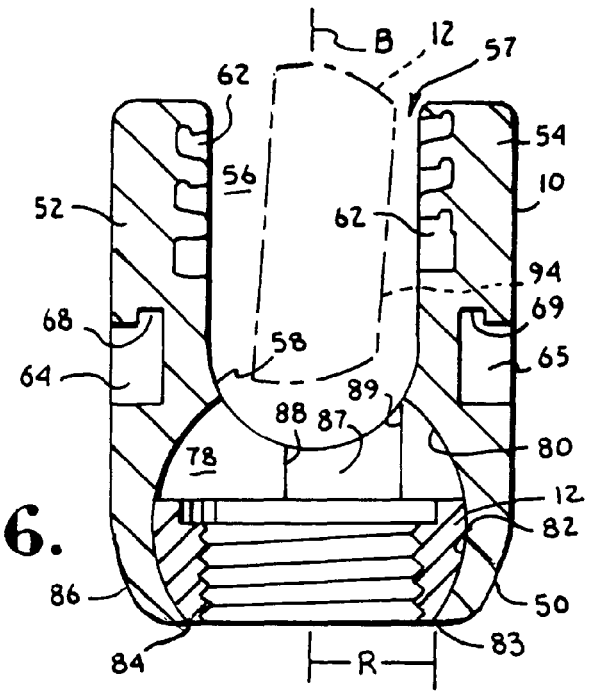
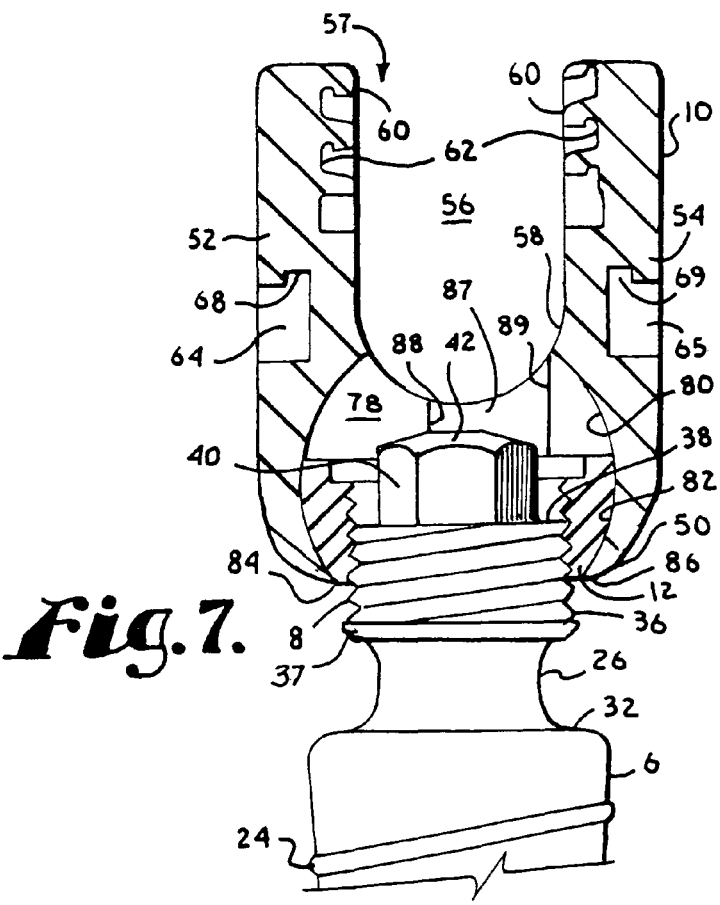

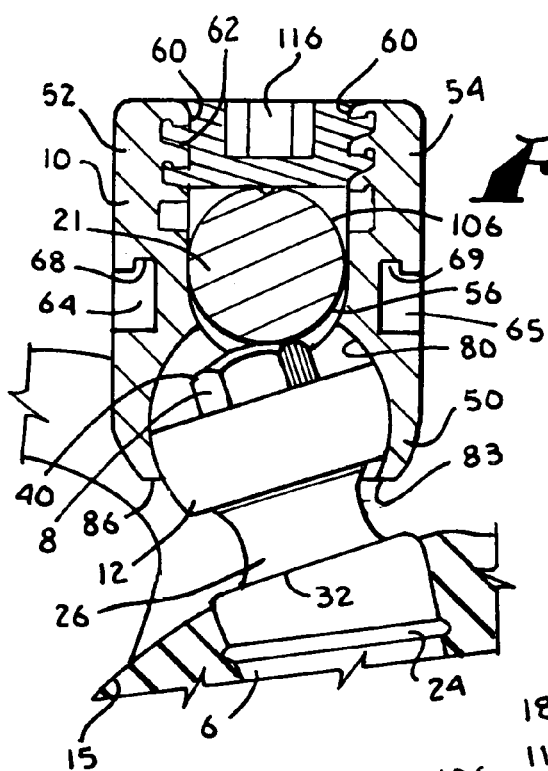
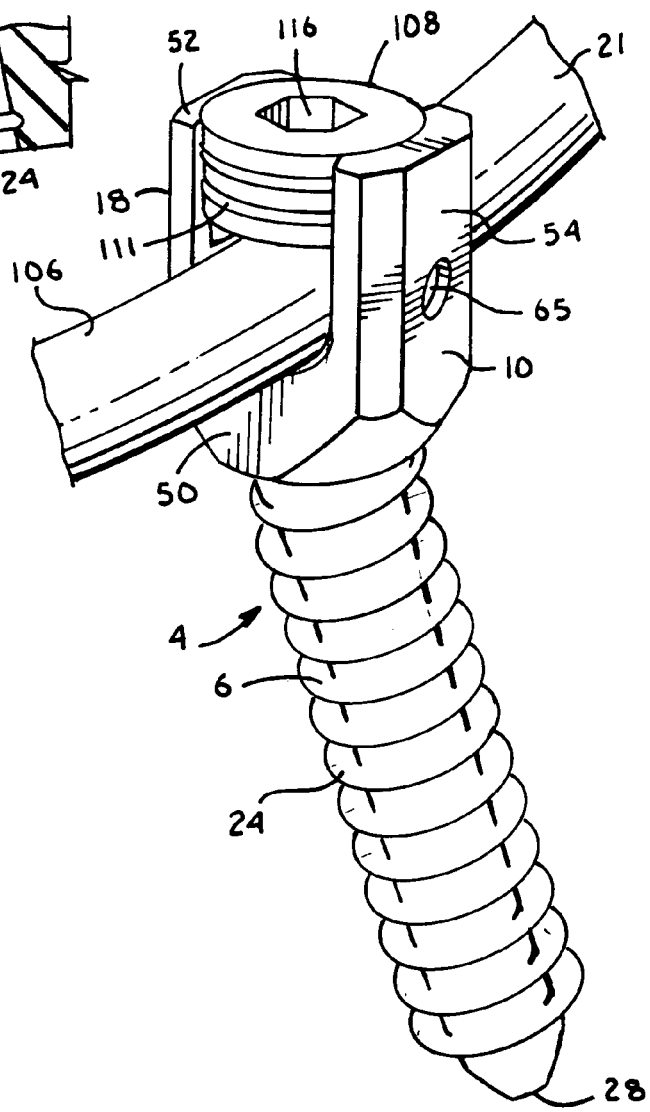

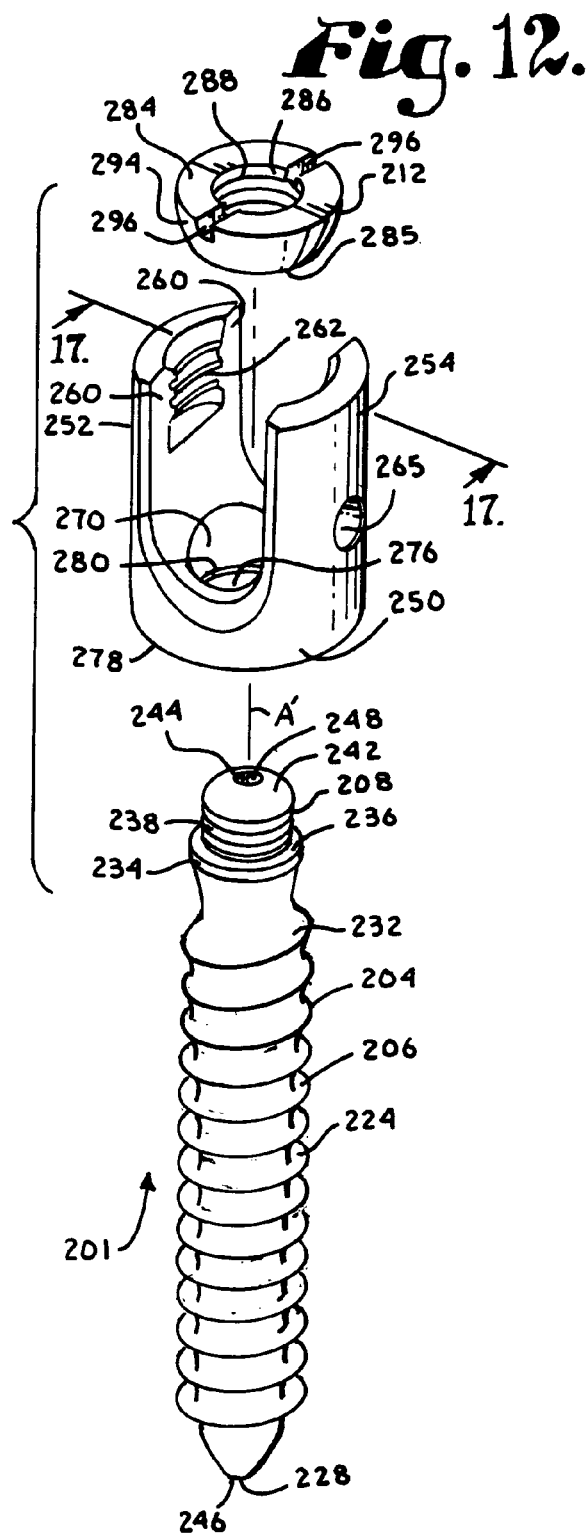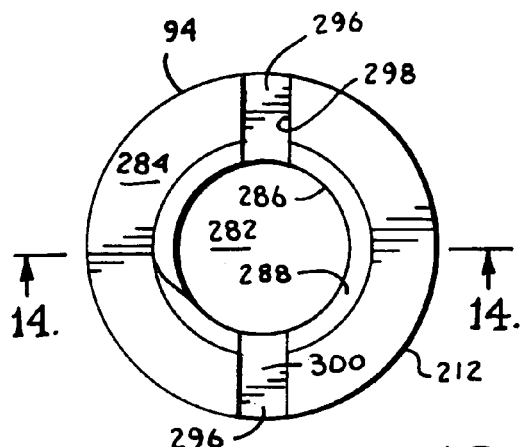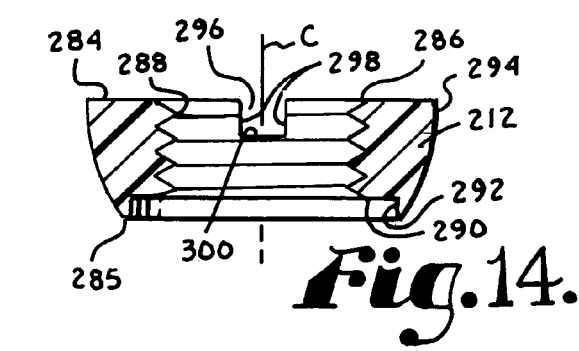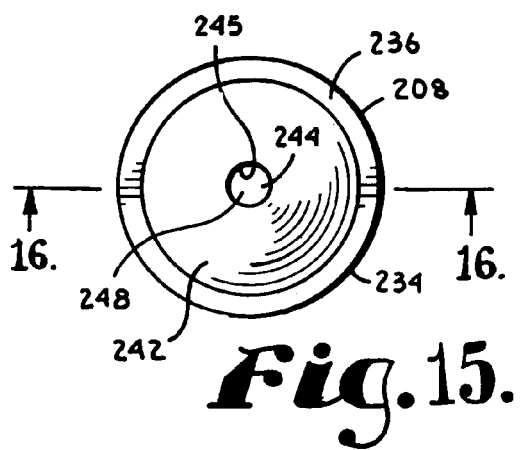

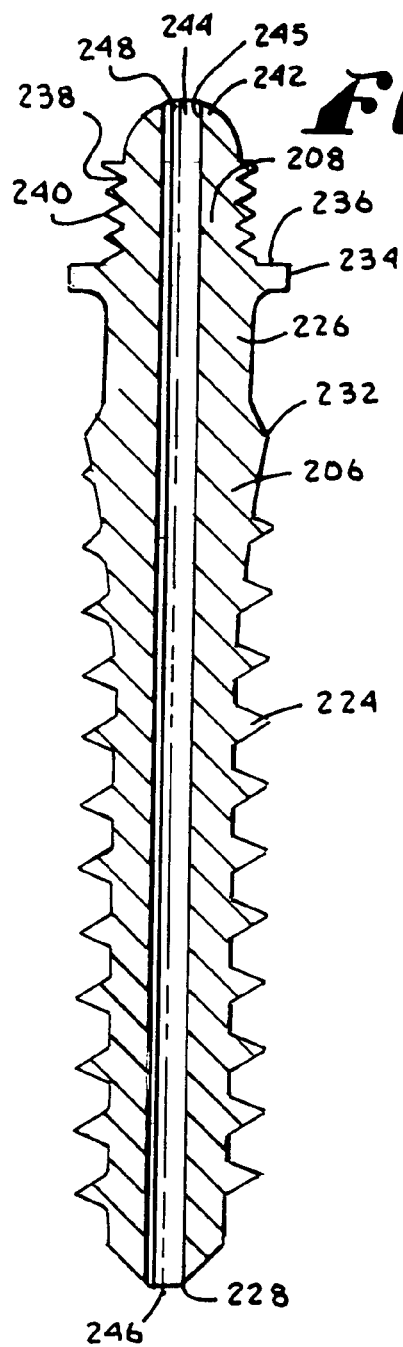
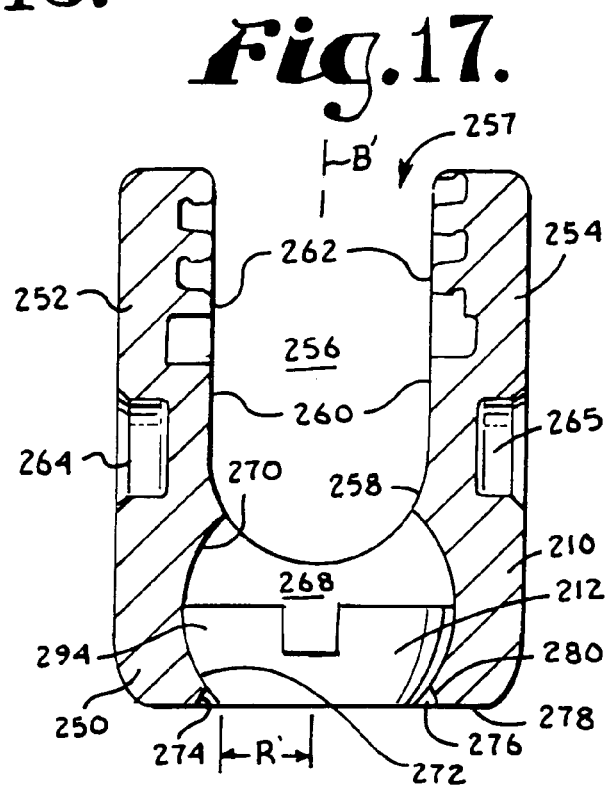
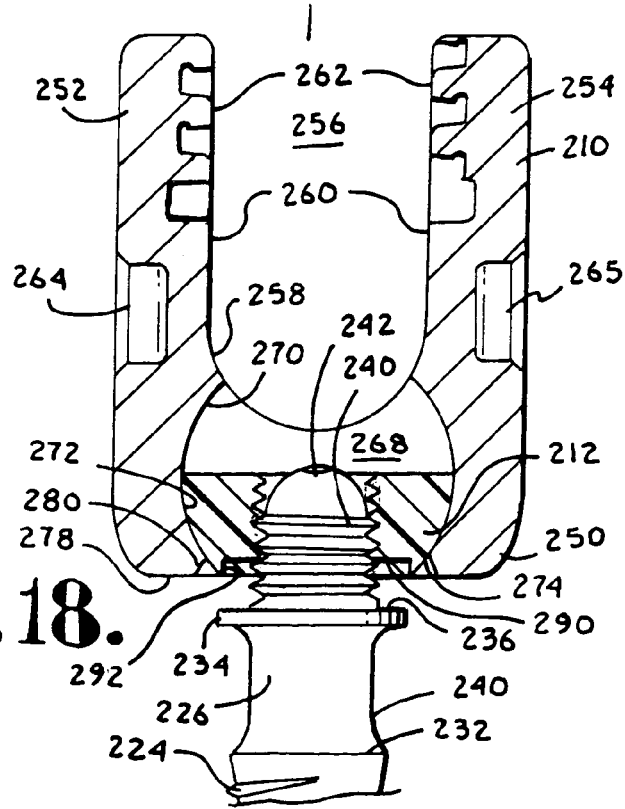

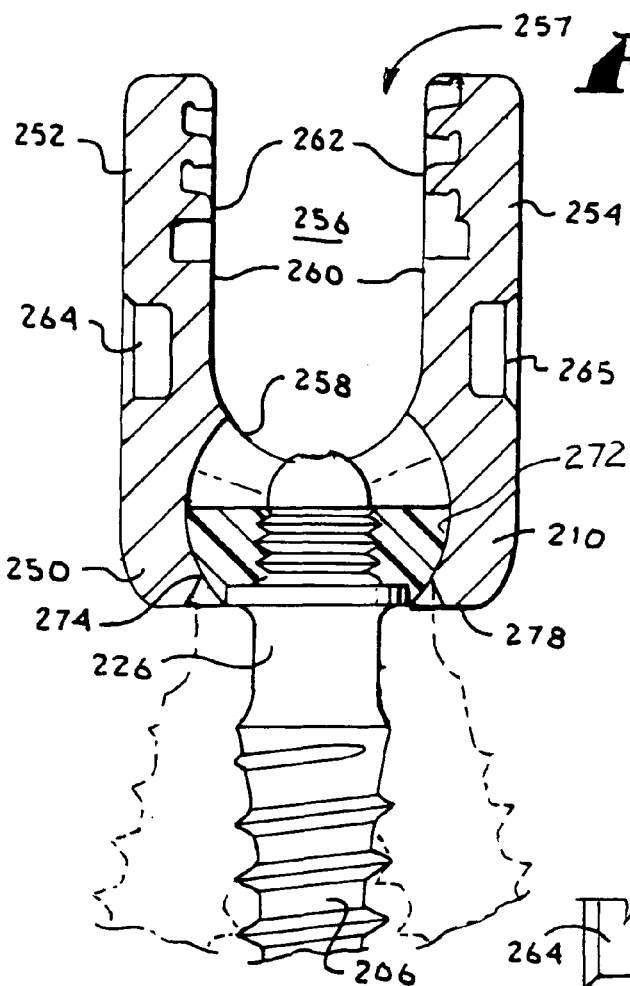
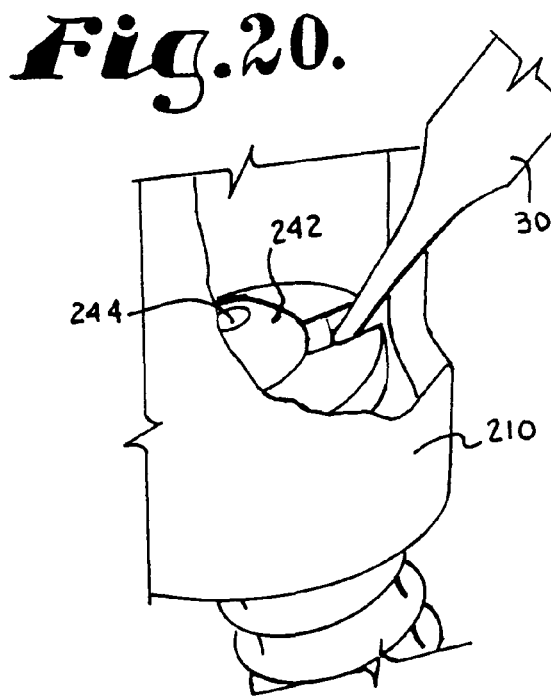
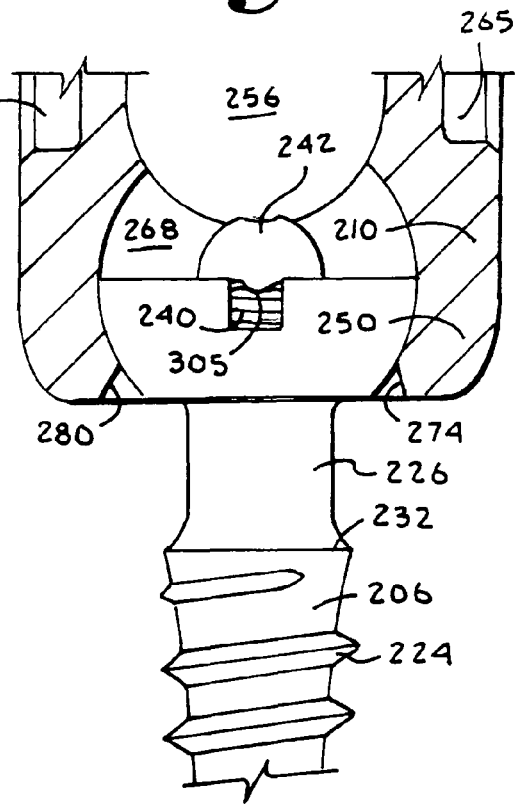

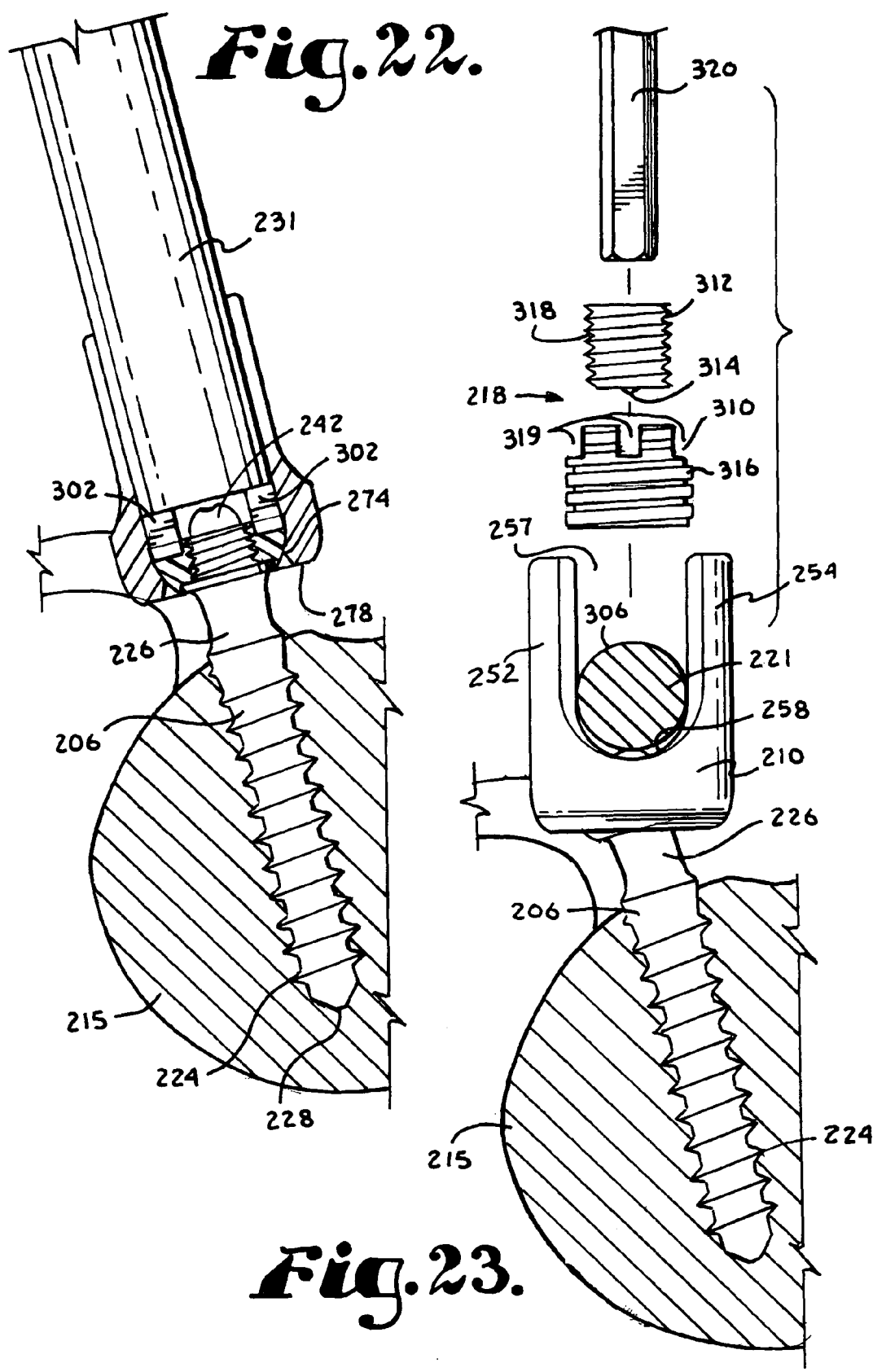

POLYAXIAL BONE SCREW WITH HELICALLY WOUND CAPTURE CONNECTION

BACKGROUND OF THE INVENTION

The present invention is directed to polyaxial bone screws for use in bone surgery, particularly spinal surgery. Such screws have a head that can swivel about a shank of the bone screw, allowing the head to be positioned in any of a number of angular configurations relative to the shank.

Many spinal surgery procedures require securing various implants to bone and especially to vertebrae along the spine. For example, elongate rods are often utilized that extend along the spine to provide support to vertebrae that have been damaged or weakened due to injury or disease. Such rods must be supported by certain vertebrae and support other vertebrae.

The most common mechanism for providing vertebral support is to implant bone screws into certain bones which then in turn support the rod or are supported by the rod. Bone screws of this type may have a fixed head relative to a shank thereof. In the fixed bone screws, the head cannot be moved relative to the shank and the rod must be favorably positioned in order for it to be placed within the head. This is sometimes very difficult or impossible to do. Therefore, polyaxial bone screws are commonly preferred.

Polyaxial bone screws allow rotation of the head about the shank until a desired rotational position of the head is achieved relative to the shank. Thereafter, a rod can be inserted into the head and eventually the head is locked or fixed in a particular position relative to the shank.

A variety of polyaxial or swivel-head bone screw assemblies are available. One type of bone screw assembly includes an open head that allows for placement of a rod within the head. A closure top or plug is then used to capture the rod in the head of the screw.

Because such implants are for placement within the human body, it is desirable for the implant to have as little effect on the body as possible. Consequently, heavy, bulky implants are undesirable and lighter implants with a relatively small profile both in height and width are more desirable. However, a drawback to smaller, lighter implants is that they may be more difficult to rigidly fix to each other and into a desired position. Lack of bulk may also mean lack of strength, resulting in slippage under high loading. Also, more component parts may be required to rigidly fix the implant in a desired position. A further drawback of smaller components is that they may be difficult to handle during surgery because of their small size, failing to provide adequate driving or gripping surfaces for tools used to drive the shank into bone.

One undesirable attribute of some of the swivel-head implants is the need for a multitude of components that may loosen or even disassemble within the body. It is most undesirable for components to be free to move around in the body after the completion of surgery. Loosening of components relative to each other may result in related undesirable movement of the bone or vertebra that the implant was intended to stabilize.

SUMMARY OF THE INVENTION

It is an object of the invention to overcome one or more of the problems described above. Further objects of the invention include: providing a polyaxial bone screw with features that provide adequate frictional or gripping surfaces for bone implantation tools and may be readily, securely fastened to each other and to bone. Also, if the implant should slip or become loose for some reason, an object of the invention is to provide an implant wherein all of the parts remain together and do not separate. Furthermore, it is an object of the invention to provide a lightweight, low profile polyaxial bone screw that assembles in such a manner that the components cooperate to create an overall structure that prevents unintentional disassembly.

A polyaxial bone screw assembly of the present invention includes a shank having a body for fixation to a bone. Integral with the shank and extending axially upwardly and outwardly therefrom is a capture structure. The capture structure has a radially projecting outer surface that is substantially cylindrical and that further includes a helically wound structure, such as a thread. The upper end of the shank is convexly curved.

The bone screw assembly further includes a head having a top portion and a base. The top portion is open and has a channel. The base also is upwardly open and includes an inner seating surface partially defining a cavity and has a lower aperture or opening. The channel of the top portion communicates with the cavity, which in turn communicates with an exterior of the base of the head through the base opening. The base opening is sized and shaped to receive the capture structure of the shank into the head cavity.

The bone screw assembly also includes an integral one piece contiguously closed ring-like retainer structure that has an internal surface with a helically wound structure thereon, such as a thread. The thread of the retainer structure is sized and shaped to mate with the thread of the shank capture structure when the retainer structure and the capture structure are coaxially aligned within the head cavity, thereby securing the retainer structure to the capture structure.

The external surface of the retainer structure is configured to be in slidable mating engagement with the surface defining the cavity of the head. Preferably, the retainer structure external surface and the mating head inner surface are substantially spherical. However, it is noted that the mating surfaces may be of another shape, such as conical or tapered, especially for the head cavity inner surface. The cooperating shapes of the retainer external surface and the head inner surface enable selective angular positioning of the shank body with respect to the head.

In one embodiment according to the invention, the capture structure includes a tool engagement formation that extends or projects from the capture structure and is located between the curved upper end and the threaded cylindrical portion thereof. In another embodiment of the invention, the closed ring-like retainer structure includes a tool engagement formation. In both embodiments, the tool formation is for non-slip engagement by a tool for driving the shank into bone and may also be cooperatively used for attaching the retainer structure to the capture structure.

Also according to the invention are tool seating surfaces that may be disposed on one or both of the capture structure and the retainer structure. In one embodiment, the shank capture structure includes tool engagement surfaces that are positioned and shaped to receive a socket type tool and a planar, tool seating surface extending radially from the lower end of the tool engagement surfaces. The seating surface is disposed coaxially with the shank body. The retainer structure has mating seating surfaces that cooperate with the shank capture structure seating surface. The tool seating surfaces and the tool engagement surfaces partially define a recess for receiving a driving tool mating with the tool engagement surfaces. When engaged, the driving tool is in contact with the capture structure tool seating surface, providing greater mating surface to the capture structure tool engagement surfaces so as to provide additional surface for frictional gripping when the shank body is driven into bone, especially harder bone.

In certain embodiments a tool seating and partially surrounding surface may be disposed on the retainer structure according to the invention such that when the retainer structure is mated with the capture structure, the retainer structure seating surface extends radially from the lower end of the tool engagement surfaces and is disposed coaxially with respect to the shank body.

In certain embodiments, both the capture structure and the retainer structure may include tool seating surfaces that extend radially in the same plane when the capture structure and the retainer structure are mated. In such embodiments, the two tool seating surfaces and the shank tool engagement surfaces partially define a recess for receiving a driving tool engaged with the tool engagement surfaces. When engaged, the driving tool is in contact with both tool seating surfaces, thereby seating the tool lower relative to the tool engagement surfaces and providing additional frictional gripping surface when the shank body is driven into bone.

A polyaxial bone screw assembly method according to the invention includes inserting an independent closed ring-like retainer into a head cavity, inserting a capture structure of a bone screw shank through a shank receiving opening of the head and into a cavity thereof; and attaching the capture structure to the retainer structure within the head.

A method according to the invention further includes driving the shank body into bone by rotating the shank body with a tool engaged with a tool engagement formation, such as a pair of aligned and spaced slots, disposed on the capture structure or the retainer structure. Further assembly steps according to the invention include inserting a rod into the channel; and biasing the rod against a top of the bone screw shank capture structure by rotatably inserting a closure member structure within or onto a mating structure of the rod receiving channel structure.

It is to be understood that while certain forms of the present invention have been illustrated and described herein, it is not to be limited to the specific forms or arrangement of parts described and shown.

Other objects and advantages of this invention will be apparent to those skilled in the art from the following description taken in conjunction with the drawings and the appended claims.

The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly according to the present invention having a shank with a capture structure at one end thereof, a head, and a closed ring-like retainer structure and further showing a rod and closure structure.

FIG. 2 is an enlarged top plan view of the retainer structure of FIG. 1.

FIG. 3 is an enlarged cross-sectional view of the retainer structure of FIG. 2, taken along line 3-3 of FIG. 2.

FIG. 4 is an enlarged top plan view of the shank of FIG. 1.

FIG. 5 is an enlarged cross-sectional view of the shank, taken along line 5-5 of FIG. 4.

FIG. 6 is an enlarged cross-sectional view of the head, taken along the line 6-6 of FIG. 1, and showing the retainer structure seated in the head (in solid lines) and illustrating the retainer structure being inserted into the head (in dashed lines).

FIG. 7 is an enlarged cross-sectional view of the head and retainer structure similar to FIG. 6, showing the shank capture structure partially threaded into the retainer structure.

FIG. 10 is an enlarged, fragmentary cross-sectional view of the head, rod and vertebra, similar to FIG. 8 and further showing the closure member structure in contact with the rod and the rod in contact with the capture structure.

FIG. 11 is a fragmentary and enlarged perspective view of the assembly of FIG. 1 shown completely assembled.

FIG. 12 is an exploded perspective view of an alternative embodiment of a polyaxial bone screw assembly according to the present invention having a shank with an upper capture structure, a head, and a closed ring-like retainer structure.

FIG. 13 is an enlarged top plan view of the retainer structure of FIG. 12.

FIG. 14 is an enlarged cross-sectional view of the retainer structure of FIG. 13, taken along line 14-14 of FIG. 13.

FIG. 15 is an enlarged top plan view of the shank of FIG. 12.

FIG. 16 is an enlarged cross-sectional view of the shank of FIG. 12, taken along line 16-16 of FIG. 15.

FIG. 17 is an enlarged cross-sectional view of the head of FIG. 12 showing the retainer structure seated in the head, taken along line 17-17 of FIG. 12.

FIG. 18 is an enlarged cross-sectional view of the head and retainer structure similar to FIG. 17, showing the shank capture structure partially assembled with respect to the retainer structure.

FIG. 19 is an enlarged cross-sectional view of the head and retainer structure, similar to FIG. 18, illustrating the shank and retainer structure being pivotable to selected angles relative to the head in solid and phantom lines.

FIG. 20 is an enlarged and fragmentary perspective view, similar to FIG. 19, illustrating the use of a punch tool to lock the position of the retainer structure relative to the capture structure.

FIG. 21 is an enlarged and partial view similar to FIG. 20 showing a thread of the capture structure deformed to rigidly secure the retainer structure to the capture structure.

FIG. 22 is an enlarged cross-sectional view of a vertebra, and the head and retainer structure of FIG. 12, showing the shank being implanted into the vertebra using a driving tool mounted on the shank capture structure and the retainer structure.

FIG. 23 is an exploded fragmentary, partially cross-sectional view of the embodiment of FIG. 12, showing a rod in contact with the domed upper extension of the capture structure and illustrating a two-piece closure member structure and driving tool for biasing the rod against the domed upper extension of the capture structure.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 8:
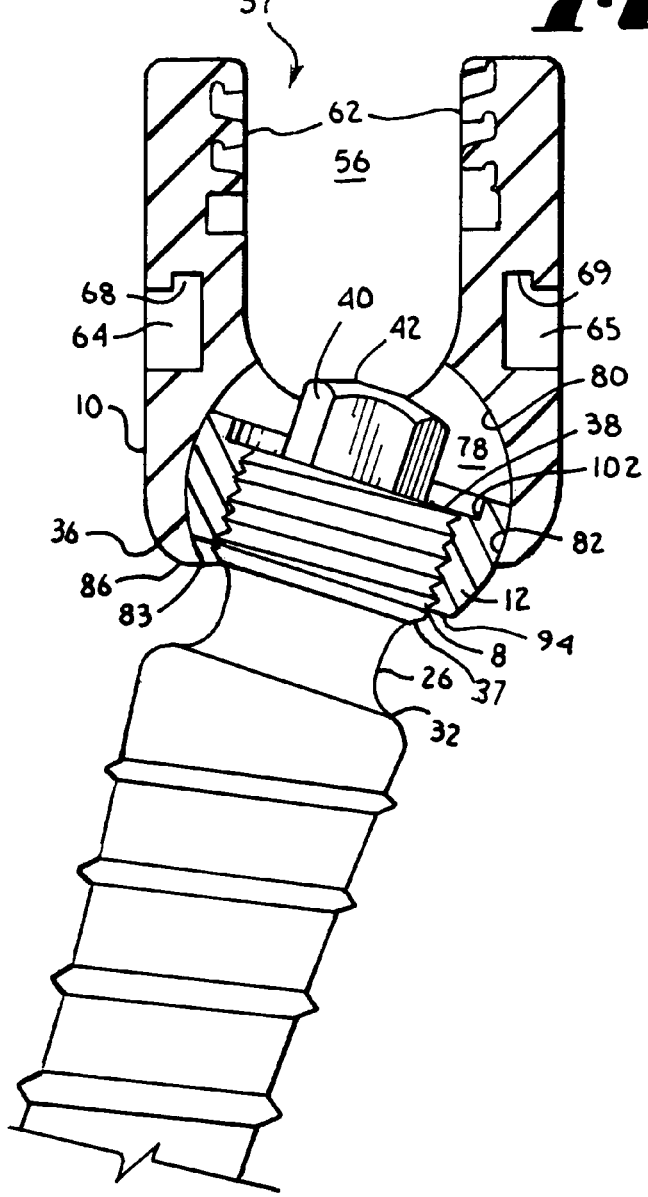
FIG. 8 is an enlarged cross-sectional view of the head and retainer structure similar to FIG. 7, illustrating the fully assembled shank and retainer structure pivoted to a selected angle relative to the head.
Figure 9:
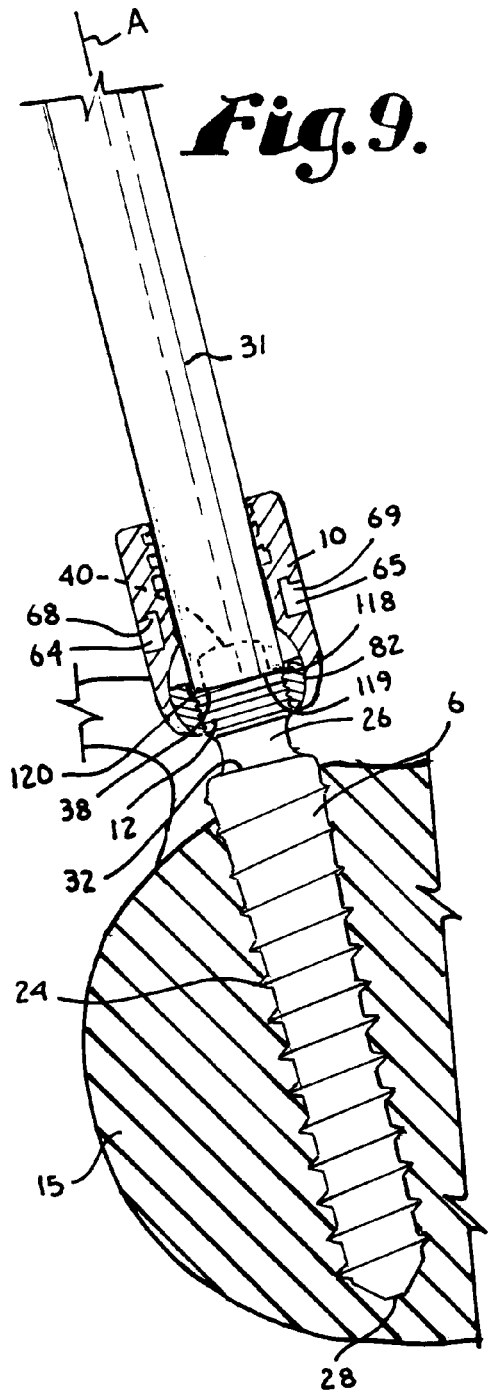
FIG. 9 is an enlarged cross-sectional view of a vertebra, and head and retainer similar to FIG. 7, showing the shank being implanted into the vertebra using a driving tool mounted on the shank capture structure.

In FIGS. 1-11 the reference number 1 generally represents a first embodiment of a polyaxial bone screw apparatus or assembly according to the present invention. The assembly 1 includes a shank 4 that further includes a body 6 integral with an upwardly extending capture structure 8; a head 10; and a closed integral retainer structure or ring 12. The shank 4, head 10 and retainer structure 12 preferably are assembled prior to implantation of the shank body 6 into a vertebra 15, which procedure is shown in FIG. 9.

FIG. 1 further shows a closure structure 18 of the invention for biasing a longitudinal member such as a rod 21 against the capture structure 8 which biases the ring 12 into fixed frictional contact with the head 10, so as to fix the rod 21 relative to the vertebra 15. The head 10 and shank 4 cooperate in such a manner that the head 10 and shank 4 can be secured at any of a plurality of angles, articulations or rotational alignments relative to one another and within a selected range of angles both from side to side and from front to rear, to enable flexible or articulated engagement of the head 10 with the shank 4 until both are locked or fixed relative to each other near the end of an implantation procedure.

The shank 4, best illustrated in FIGS. 1 and 5, is elongate, with the shank body 6 having a helically wound bone implantable thread 24 extending from near a neck 26 located adjacent to the capture structure 8 to a tip 28 of the body 6 and extending radially outward therefrom. During use, the body 6 utilizing the thread 24 for gripping and advancement is implanted into the vertebra 15 leading with the tip 28 and driven down into the vertebra 15 with an installation or driving tool 31, so as to be implanted in the vertebra 15 to near the neck 26, as shown in FIG. 9, and as is described more fully in the paragraphs below. The shank 4 has an elongate axis of rotation generally identified by the reference letter A. It is noted that any reference to the words top, bottom, up and down, and the like, in this application refers to the alignment shown in the various drawings, as well as the normal connotations applied to such devices, and is not intended to restrict positioning of the assembly 1 in actual use.

The neck 26 extends axially outward and upward from the shank body 6. The neck 26 is of reduced radius as compared to an adjacent top 32 of the body 6. Further extending axially and outwardly from the neck 26 is the capture structure 8 that provides a connective or capture apparatus disposed at a distance from the body top 32 and thus at a distance from the vertebra 15 when the body 6 is implanted in the vertebra 15.

The capture structure 8 is configured for connecting the shank 4 to the head 10 and capturing the shank 4 in the head 10. The capture structure 8 has an outer substantially cylindrical surface 34 having a helically wound advancement structure thereon which in the illustrated embodiment is a V-shaped thread 36 disposed adjacent to a seating surface 38 and extending to a location near a rim 37. The rim 37 is adjacent to the neck 26. Although a simple thread 36 is shown in the drawings, it is foreseen that other structures including other types of threads, such as buttress and reverse angle threads, and non threads, such as helically wound flanges with interlocking surfaces, may be alternatively used in alternative embodiments of the present invention. The cylindrical surface 34 could be truncated giving a non-contiguous helically wound structure.

The shank 4 further includes a tool engagement structure 40 disposed near a top end surface 42 thereof for engagement of the driving tool 31 shown in FIG. 9 which includes a driving structure in the form of a socket. The tool 31 is configured to fit about the tool engagement structure 40 so as to form a socket and mating projection for both driving and rotating the shank body 6 into the vertebra 15. Specifically in the embodiment shown in FIGS. 1-11, the tool engagement structure 40 is in the shape of a hexagonally shaped extension head coaxial with both the threaded shank body 6 and the threaded capture structure 8.

The top end surface 42 of the shank 4 is preferably curved or dome-shaped as shown in the drawings, for contact engagement or positive mating engagement with the rod 21, when the bone screw assembly 1 is assembled, as shown in FIGS. 10 and 11 and in any alignment of the shank 4 relative to the head 10. In certain embodiments, the surface 42 is smooth. While not required in accordance with practice of the invention, the surface 42 may be scored or knurled to further increase frictional positive mating engagement between the surface 42 and the rod 21.

The shank 4 shown in the drawings is cannulated, having a small central bore 44 extending an entire length of the shank 4 along the axis A. The bore 44 is defined by an inner cylindrical wall 45 of the shank 4 and has a first circular opening 46 at the shank tip 28 and a second circular opening 48 at the top surface 42. The bore 44 is coaxial with the threaded body 6 and the capture structure outer surface 34. The bore 44 provides a passage through the shank 4 interior for a length of wire (not shown) inserted into the vertebra 15 prior to the insertion of the shank body 6, the wire providing a guide for insertion of the shank body 6 into the vertebra 15.

Referring to FIGS. 1 and 6 through 10, the head 10 has a generally U-shaped appearance with a partially cylindrical inner profile and a faceted outer profile; however, the outer profile could also be partially cylindrical. The head 10 includes a somewhat spherical base 50 integral with a pair of upstanding arms 52 and 54 forming a U-shaped cradle and defining a U-shaped channel 56 between the arms 52 and 54 with an upper opening 57 and a lower seat 58 having substantially the same radius as the rod 21 for operably snugly receiving the rod 21.

Each of the arms 52 and 54 has an interior surface 60 that defines the inner cylindrical profile and includes a partial helically wound guide and advancement structure 62. In the illustrated embodiment, the guide and advancement structure 62 is a partial helically wound interlocking flangeform configured to mate under rotation with a similar structure on the closure top 18, as described more fully below. However, it is foreseen that the guide and advancement structure 62 could alternatively be a V-shaped thread, a buttress thread, a reverse angle thread or other thread like or non-thread like helically wound advancement structures for operably guiding under rotation and advancing the closure top downward between the arms 52 and 54.

Tool engaging apertures 64 and 65 are formed within the arms 52 and 54, respectively which may be used for holding the head 10 during assembly with the shank 4 and the retainer structure 12 and also during the implantation of the shank body 6 into a vertebra 15.

Communicating with the apertures 64 and 65 are respective upwardly projecting, hidden inner recesses 68 and 69. The holding tool (not shown) is sized and shaped to have structure to mate with and to be received in the apertures 64 and 65 and locked into place by pulling the holding tool slightly axially upward relative to the base 50 and toward the upper opening 57 of the channel 56 formed by the arms 52 and 54. The holding tool and respective apertures 64 and 65 can be configured for a flexible snap on/spring off engagement wherein the holding tool has flexible legs which splay outwardly to position the tool for engagement in the apertures 64 and 65. It is noted that the apertures 64 and 65 and the cooperating holding tool may be configured to be of a variety of sizes and locations along any of the surfaces of the arms 52 and 55, for example, extending into a face 75 or disposed only at a single face or facet.

Communicating with and located beneath the U-shaped channel 56 of the head 10 is a chamber or cavity 78 substantially defined by an inner surface 80 of the base 50, the cavity 78 opens upwardly into the U-shaped channel 56. The inner surface 80 is substantially spherical, with at least a portion thereof forming a partial internal spherical seating surface 82 having a first radius. The surface 82 is sized and shaped for mating with the retainer structure 12, as described more fully below.

The base 50 further includes a restrictive neck 83, having a second radius R and defining a bore 84 communicating with the cavity 78 and a lower exterior 86 of the base 50. The bore 84 is coaxially aligned with respect to a rotational axis B of the head 10. The neck 83 and associated bore 84 are sized and shaped to be smaller (the second radius) than a radial dimension of the retainer structure 12 (the first radius), as will be discussed further below, so as to form a restriction at the location of the neck 83 relative to the retainer structure 12, to prevent the retainer structure 12 from passing from the cavity 78 and out into the lower exterior 86 of the head 10 when the retainer structure 12 is seated.

The inner surface 80 further defines an elongate upper loading recess 87 for accommodating and loading the retainer structure 12 into the cavity 78. The loading recess 87 is generally vertically disposed in the head 10, extending between and communicating with both the channel 56 and the cavity 78, allowing for ease in top loading the retainer structure 12 into the cavity through the upper opening 57 and otherwise allowing for the spherical wall 80 of the head 10 to have a comparatively enlarged radius to allow for increased thickness and strength of the head base 50; however, the loading recess 87 is not always necessary.

The retainer structure or ring 12 is used to retain the capture structure 8 of the shank 4 within the head 10. The retainer structure 12, best illustrated by FIGS. 1-3 and 6-8, has an operational central axis that is the same as the elongate axis A associated with the shank 4, but when the retainer structure 12 is separated from the shank 4, the axis of rotation is identified as axis C, as shown in FIG. 3. The retainer structure 12 has a central bore 90 that passes entirely through the retainer structure 12 from a top surface 92 to a bottom surface 94 thereof. A first inner cylindrical surface 96 defines a substantial portion of the bore 90, the surface 96 having a helically wound advancement structure thereon as shown by a helical rib or thread 98 extending from adjacent the bottom surface 94 to adjacent a flat, seating surface 99 disposed perpendicular to the inner surface 96.

Although a simple helical rib 98 is shown in the drawings, it is foreseen that other helical structures including other types of threads, such as buttress and reverse angle threads, and non threads, such as helically wound flanges with interlocking surfaces, may be alternatively used in an alternative embodiment of the present invention. The inner cylindrical surface 96 with helical rib 98 are configured to mate under rotation with the capture structure outer surface 34 and helical advancement structure or thread 36, as described more fully below.

The retainer structure 12 further includes a second inner wall or cylindrical surface 102, coaxial with the first inner cylindrical surface 96. The surface 102 is disposed between the seating surface 99 and the top surface 92 of the retainer structure 12 and has a diameter greater than that of the cylindrical surface 96. As will be described more fully below, the cylindrical surface 102 in cooperation with the seating surface 99 and the surface 38 of the retainer structure 12, provide a recess about the base of the tool engagement structure 40 and a stable seating surface for the tool 31, as shown in FIG. 9. The wall 102 which is the outer wall of the recess may be shaped to fit an outer surface of the tool 31 and may be faceted or especially hexagonal in shape to better grip the tool 31.

The retainer structure or ring 12 has a radially outer partially spherically shaped surface 104 sized and shaped to mate with the partial spherical shaped seating surface 82 of the head and having a third radius approximately equal to the first radius associated with the surface 82. The retainer structure third radius is larger than the second radius R of the neck 83 of the head 10. Although not required, it is foreseen that the outer partially spherically shaped surface 104 may be a high friction surface such as a knurled surface or the like.

The elongate rod or longitudinal member 21 that is utilized with the assembly 1 can be any of a variety of implants utilized in reconstructive spinal surgery, but is normally a cylindrical elongate structure having a cylindrical surface 106 of uniform diameter and having a generally smooth surface. The rod 21 is preferably sized and shaped to snugly seat near the bottom of the U-shaped channel 56 of the head 10 and, during normal operation, is positioned slightly above the bottom of the channel 56 at the lower seat 58. In particular, the rod 21 normally directly or abuttingly engages the shank top surface 42, as shown in FIG. 10 and is biased against the dome shank top surface 42, consequently biasing the shank 4 downwardly in a direction toward the base 50 of the head 10 when the assembly 1 is fully assembled. For this to occur, the shank top surface 42 must extend at least slightly into the space of the channel 56 when the retainer structure 12 is snugly seated in the lower part of the head cavity 80. The shank 4 and retainer structure 12 are thereby locked or held in position relative to the head 10 by the rod 21 firmly pushing downward on the shank top surface 42.

With reference to FIGS. 1, 10 and 11, the closure structure or closure top 18 can be any of a variety of different types of closure structures for use in conjunction with the present invention with suitable mating structure on the upstanding arms 52 and 54. In the embodiment shown, the closure top 18 is rotatably received between the spaced arms 52 and 54.

The illustrated closure top 18 has a generally cylindrical shaped base 108 with an upwardly extending break-off head 110. The base 108 includes a helically wound guide and advancement structure 111 that is sized, shaped and positioned so as to engage and interlock with the guide and advancement structure 62 on the arms 52 and 54 to provide for rotating advancement of the closure structure 18 into the head 10 when rotated clockwise and, in particular, to cover the top or upwardly open portion of the U-shaped channel 56 to capture the rod 21, preferably without splaying of the arms 52 and 54. The closure structure 18 also operably biases against the rod 21 by advancement and applies pressure to the rod 21 under torquing, so that the rod 21 is urged downwardly against the shank top end surface 42 that extends up into the channel 56. Downward biasing of the shank top surface 42 operably produces a frictional engagement between the rod 21 and surface 42 and also urges the retainer structure 12 toward the base 50 of the head 10, so as to frictionally seat the retainer structure external spherical surface 104 fixedly against the partial internal spherical seating surface 82 of the head 10, also fixing the shank 4 and retainer structure 12 in a selected, rigid position relative to the head 10.

In the embodiment shown, the closure structure includes a break-off head 110 secured to the base 108 at a neck 114 that is sized and shaped so as to break away at a preselected torque that is designed to properly seat the retainer structure 12 in the head 10. The break-off head 110 includes an external faceted surface 115 that is sized and shaped to receive a conventional mating socket type head of a driving tool (not shown) to rotate and torque the closure structure 18. The break-off head 110 also includes a central bore 117 and grooves 118 for operably receiving manipulating tools.

The closure structure 18 also includes removal tool engagement structure which in the present embodiment is in the form of a hex-shaped and axially aligned aperture 116 disposed in the base 108, as shown in FIGS. 10 and 11. The hex aperture 116 is accessible after the break-off head 110 breaks away from the base 108. The aperture 116 is coaxial with the helically wound guide and advancement structure 111 and is designed to receive a hex tool, of an Allen wrench type, into the aperture 116 for rotating the closure structure base 108 subsequent to installation so as to provide for removal thereof, if necessary. Although a hex-shaped aperture 116 is shown in the drawings, the tool engagement structure may take a variety of tool-engaging forms and may include one or more apertures of various shapes, such as a pair of spaced apart apertures, or a left hand threaded bore, or an easyout engageable step down bore, or a Torx aperture, or a multi-lobular aperture or the like.

Prior to the polyaxial bone screw assembly 1 being placed in use according to the invention, the ring-like retainer structure 12 is typically first inserted or top-loaded, into the head U-shaped channel 56, as is shown in dotted lines in FIG. 6, and then into the cavity 78 through the vertical loading recess 87 to dispose the structure 12 within the inner surface 80 of the head 10. Then, the retainer structure 12 is rotated approximately 90 degrees so as to be coaxial with the head 10 and then seated in sliding engagement with the seating surface 82 of the head 10, also shown in FIG. 6.

With reference to FIG. 7, the shank capture structure 8 is then inserted or bottom-loaded into the head 10 through the bore 84 defined by the neck 83. The retainer structure 12, now disposed in the head 10 is coaxially aligned with the shank capture structure 8 so that the helical advancement structure 36 rotatingly mates with the helical advancement structure 98 of the retainer structure 12.

The shank 4 and or the retainer structure 12 are rotated to fully mate the structures 36 and 98 along the respective cylindrical surfaces 34 and 96, as shown in FIG. 7, fixing the capture structure 8 to the retainer structure 12, until the seating surface 38 and the seating surface 99 are contiguous and disposed in the same plane and the rim 37 abuts the surface 94 of the retainer structure 12 as shown in FIG. 8. Permanent, rigid engagement of the capture structure 8 to the retainer structure 12 may be further ensured and supported by the use of adhesive, a spot weld, deforming one or both threads with a punch or the like.

As shown in FIG. 8, at this time the shank 4 is in slidable and rotatable engagement with the head 10, while the capture structure 8 and the lower aperture or neck 83 of the head 10 cooperate to maintain the shank body 6 in rotational relation with the head 10. According to the embodiment of the invention shown in FIGS. 1-11, only the retainer structure 12 is in slidable engagement with the head spherical seating surface 82. Both the capture structure 12 and threaded portion of the shank body 6 are in spaced relation with the head 10.

It is believed that an advantage to this embodiment is that, although the shank 6 could engage the head lower aperture or neck 83 when rotated fully relative to the head 10 as best illustrated in FIG. 8, upper shank body 6 does not contact the lower spherical seating surface 82, so that rotational stresses between the capture structure 8 and the retainer structure 12 are lessened, making it less likely that the retainer structure 12 would loosen from the capture structure 8 or that the capture structure would fail or break when the assembly 1 is implanted and loaded.

An extent of rotation is shown in FIG. 8 where it is illustrated that the shank body 6 can be rotated through a substantial angular rotation relative to the head 10, both from side to side and from front to rear so as to substantially provide a universal or ball joint wherein the angle of rotation is only restricted by engagement of the neck 26 of the shank body 6 with the neck or lower aperture 83 of the head 10.

With reference to FIG. 9, the assembly 1 is then typically screwed into a bone, such as the vertebra 15, by rotation of the shank 4 using the driving tool 31 that operably drives and rotates the shank 4 by engagement thereof with the hexagonally shaped extension head 40 of the shank 4. Preferably, when the driving tool 31 engages the head 40, an end portion 118 thereof is disposed in a recess defined by the head 40, the seating surface 38, the contiguous seating surface 99 and the inner cylindrical surface 102, with a bottom surface 119 of the tool 31 contacting and frictionally engaging both the seating surface 38 and the seating surface 99. Some frictional engagement between an outer surface 120 of the tool 31 with the cylindrical surface 102 may also be achievable during rotation of the driving tool 31.

It is foreseen that in other embodiments according to the invention, the tool engaging recess may be defined by only one of the seating surface 38 or the seating surface 99. For example, a retainer structure might not include a seating surface, so a driving tool might seat or mate only with a seating surface or an internal aperture of a shank capture structure. Alternatively, the tool engaging end of a capture structure might be of a size and shape that a driving tool substantially seats on a seating surface of a retainer structure or ring and not the capture structure.

Typically, the head 10 and the retainer structure 12 are assembled on the shank 4 before inserting the shank body 6 into the vertebra 15, but in certain circumstances, the shank body 6 can be first partially implanted in the bone with the capture structure 8 extending proud to allow assembly with the head 10 utilizing the retainer structure 12. Then the shank body 6 can be further driven into the vertebra 15.

With reference to FIGS. 1 and 5 as well as FIG. 9, the vertebra 15 may be pre-drilled to minimize stressing the bone and have a guide wire (not shown) that is shaped for the cannula 44 inserted to provide a guide for the placement and angle of the shank 4 with respect to the vertebra 15. A further tap hole may be made using a tap with the guide wire as a guide. Then, the assembly 1 or the solitary shank 4, is threaded onto the guide wire utilizing the cannulation bore 44 by first threading the wire into the bottom opening 46 and then out of the top opening 48. The shank 4 is then driven into the vertebra 15, using the wire as a placement guide.

With reference to FIGS. 1, 10 and 11, the rod 21 is eventually positioned within the head U-shaped channel 56, and the closure structure or top 18 is then inserted into and advanced between the arms 52 and 54 so as to bias or push against the rod 21. The break-off head 110 of the closure structure 18 is twisted to a preselected torque, for example 90 to 120 inch pounds, to urge the rod 21 downwardly. The shank top end surface 42, because it is rounded to approximately equally extend upward into the channel 56 approximately the same amount no matter what degree of rotation exists between the shank 4 and head 10 and because the surface 42 is sized to extend upwardly into the U-shaped channel 56, the surface 42 is engaged by the rod 21 and pushed downwardly toward the base 50 of the head 10 when the closure structure 18 biases downwardly toward and onto the rod 21. The downward pressure on the shank 4 in turn urges the retainer structure 12 downward toward the head seating surface 82, with the retainer structure seating surface 99 in frictional engagement with the head seating surface 82. As the closure structure 18 presses against the rod 21, the rod 21 presses against the shank and the retainer structure 12 that is now rigidly attached to the shank 4 which in turn becomes frictionally and rigidly attached to the head 10, fixing the shank body 6 in a desired angular configuration with respect to the head 10 and rod 21.

FIG. 10 illustrates the polyaxial bone screw assembly 1 and including the rod 21 and the closure structure 18 positioned in a vertebra 15. The axis A of the bone shank 4 is illustrated as not being coaxial with the axis B of the head 10 and the shank 4 is fixed in this angular locked configuration. Other angular configurations can be achieved, as required during installation surgery due to positioning of the rod 21 or the like.

If removal of the assembly 1 and associated rod 21 and closure structure 18 is necessary, disassembly is accomplished by using a driving tool of an Allen wrench type (not shown) mating with the aperture 116 and turned counter-clockwise to rotate the base 108 and reverse the advancement thereof in the head 10. Then, disassembly of the assembly 1 is accomplished in reverse order to the procedure described previously herein for assembly.

With reference to FIGS. 12-25, the reference number 201 generally represents a second or alternative embodiment of a polyaxial bone screw apparatus or assembly according to the present invention. As shown in FIG. 12, the assembly 201 includes a shank 204 that has a body 206 integral with a capture structure 208, a head 210, and a retainer structure 212. The shank 204, head 210 and retainer structure 212 are typically assembled prior to implantation of the shank body 206 into a vertebra 215, as shown in FIGS. 18-22.

FIG. 23 further shows a closure assembly 218 of the invention for biasing a longitudinal member such as a rod 221 against the capture structure 208 so as to fix the rod 221 relative to the vertebra 215.

Similar to the embodiment shown in FIGS. 1-11, the alternative embodiment of the invention 201 provides for the head 210 and shank 204 to cooperate in such a manner that the head 210 and shank 204 can be secured at any of a plurality of obtuse angles, relative to one another and within a selected range of angles both side to side and front to rear, to enable flexible engagement of the assembly 201 with the rod 221, as shown in FIG. 19, and will be described in more detail below. That is the two elements, the head 210 and the shank 204, are articulatable or rotatable relative to each other within a preselected range of movement until locked in a fixed configuration at the end of the procedure.

The shank 204, best illustrated in FIGS. 12 and 16 is elongate, with the shank body 206 having a helically wound bone implantable thread 224 extending from near a neck 226 located adjacent to the capture structure 208 to a tip 228 of the body 206 and extending radially outward therefrom. During use, the body 206 utilizing the thread 224 is implanted into the vertebra 215 leading with the tip 228 and driven down into the bone with an installation tool 231 to adjacent the neck 226 as shown in FIG. 22, described more fully in the paragraphs below. The shank 204 has an elongate axis of rotation generally identified by the reference letter A'.

The neck 226 extends axially outward and upward from the shank body 206. The neck 226 constricts to a reduced radius as compared to an adjacent top 232 of the body 206. Further extending axially and outwardly from the neck 226 is the capture structure 208 that provides a connective or capture apparatus disposed at a distance from the shank body top 232 and thus at a distance from the vertebra 215 when the body 206 is implanted in the vertebra 215. The capture structure 208 is configured for connecting the shank 204 with the head 210 and the retainer structure 212.

The capture structure 208 includes an outer substantially cylindrical surface 234 contiguous to the neck 226 and coaxial with the shank body 206. The cylindrical surface 234 is also contiguous and disposed substantially perpendicular to a seating surface 236. The seating surface 236 is also coaxial with the shank body 206 and the cylindrical surface 234. Both the cylindrical surface 234 and the seating surface 236 are configured to come into frictional engagement with the retainer structure 212, as described more fully below.

Perpendicular to and contiguous with the seating surface 236 is a second cylindrical surface 238 having a helically wound advancement structure thereon as shown by a helical rib or thread 240 extending from adjacent the seating surface 236 to adjacent a rod engagement dome 242. Although a simple helical rib 240 is shown in the drawings, it is foreseen that other helical structures including other types of threads, such as buttress and reverse angle threads, and non threads, such as helically wound flanges with interlocking surfaces, may be alternatively used in an alternative embodiment of the present invention.

Figure 24:
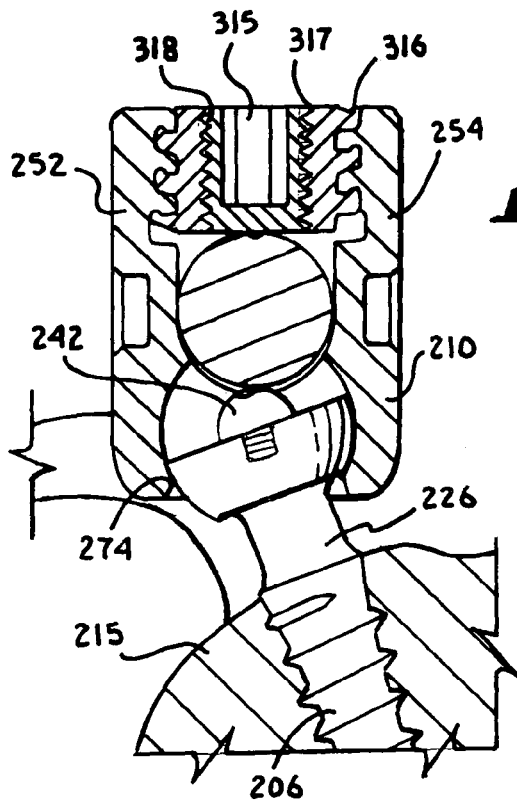
FIG. 24 is an enlarged cross-sectional view of the assembly of FIG. 23 shown completely assembled.
Figure 25:
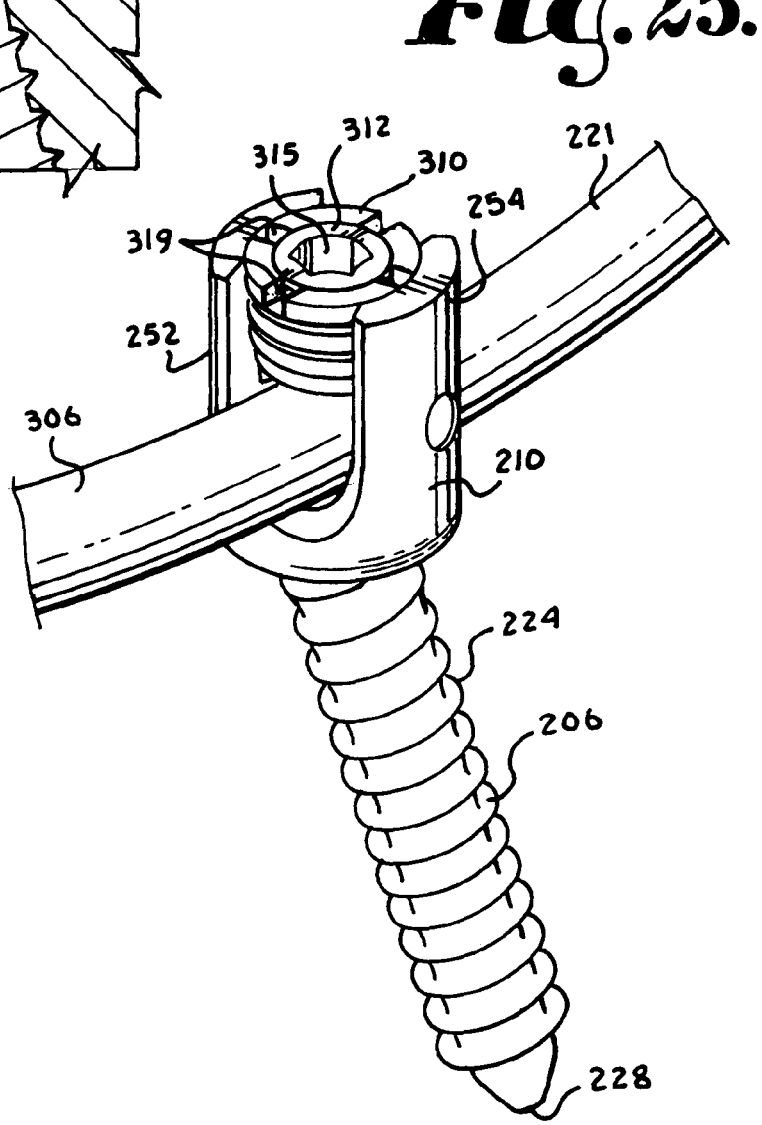
FIG. 25 is an enlarged perspective view of the assembly of FIG. 23 shown completely assembled.

The top end surface or dome 242 of the shank 204 is preferably convex, domed or curved as shown in the drawings, and sized and positioned for positive engagement with the rod 221 when the bone screw assembly 201 is assembled, as shown in FIGS. 24 and 25. If desired, the dome 242 may be scored or knurled. In certain embodiments, the purpose of the dome 242 is simply to be engaged by the rod 221 during assembly and be biased downwardly in such a manner as to frictionally engage the retainer structure 212, which is secured to the shank 206 at this time, within the head 210, as described below. The dome 242 may be radiused so that the dome 242 engages the rod 221 at generally the same level or height relative to the head channel lower surface 258, even as the head 210 is swivelled relative to the shank 204. However in other embodiments the dome 242 can have other shapes.

In the embodiment shown in FIGS. 12-25, the shank body 206 and capture structure 208 components are integral. Furthermore the shank 204 is cannulated, having a small cylindrical central bore 244 extending an entire length of the shank 204 along the axis A'. The bore 244 is defined by an inner cylindrical wall 245 of the shank 204 and has a first circular opening 246 at the shank tip 228 and a second circular opening 248 at the dome top surface 242. The bore 244 is coaxial with the threaded body 206 and capture structure outer cylindrical surfaces 234 and 238. The bore 244 provides a passage through the shank 204 interior for a length of wire (not shown) inserted into the vertebra 215 prior to the insertion of the shank body 206, the wire providing a guide for accurate insertion of the shank body 206 into the vertebra 215.

Referring to FIGS. 12, 17 and 18, the head 210 is substantially cylindrical in external profile and includes a base portion 250 integral with a pair of upstanding arms 252 and 254 forming a U-shaped channel 256 between the arms 252 and 254 with an upper opening 257 and the lower surface 258 having substantially the same radius as the rod 221. In operation, the rod 221 preferably is located just above the channel lower surface 258.

Each of the arms 252 and 254 has an interior surface 260 that defines an inner cylindrical profile and includes a partial helically wound guide and advancement structure 262. Similar to the guide and advancement structure 62 shown with respect to FIGS. 1-11, the guide and advancement structure 262 is a partial helically wound flangeform configured to mate and interlock under rotation about an axis B' with a similar structure disposed on the closure top assembly 218, as described more fully below. However, it is foreseen that the guide and advancement structure 262 could alternatively be a V-shaped thread, a buttress thread, a reverse angle thread or other thread like or non-thread like helically wound advancement structures for operably guiding under rotation and advancing the closure top between the arms 252 and 254. Also, it is foreseen that this mating advancement structure could be located on the cylindrical external surfaces of the arms 252 and 254.

The head 210 includes external, closed end grip bores 264 and 265 disposed on the respective arms 252 and 254 for positive engagement by a holding tool (not shown) to facilitate secure gripping of the head 210 during assembly of the head 210 with the shank 204 and retainer structure 212. Furthermore, the grip bores 264 and 265 may be utilized to hold the head 210 during the implantation of the shank body 206 into the vertebra 215. The bores 264 and 265 are centrally located on the respective arms 252 and 254. However, it is noted that the bores 264 and 265 may be configured to be of a variety of sizes and locations along outer surfaces of the arms 252 and 254.

Communicating with the U-shaped channel 256 of the head 210 is a chamber or cavity 268 substantially defined by an inner surface 270 of the base 50, the cavity 268 opening upwardly into the U-shaped channel 256. The inner surface 270 is substantially spherical, with at least a portion thereof forming a partial internal spherical seating surface 272 having a first radius, the surface 272 for mating with the retainer structure 212, as described more fully below.

The base 250 further includes a restrictive aperture, opening or neck 274, having a second radius R' and partially defining a bore 276 communicating with the cavity 268 and a bottom exterior 278 of the base 50. The bore 276 is coaxial with a rotational axis B' of the head 210. A bevel 280 extends between the neck 274 and the bottom exterior 278. The neck 274 and associated bore 276 are sized and shaped to be smaller than a radial dimension of the retainer structure 212, as will be discussed further below, so as to form a restriction at the location of the neck 274 relative to the retainer structure 212, to prevent the structure 212 from passing between the cavity 268 and the bottom exterior 278 of the head 210, when fully seated. The bevel 280 widens the angular range of the shank 204 when assembled with the head 210.

The retainer structure or ring 212 is used to retain the capture structure 208 of the shank 204 within the head 210. The retainer structure 212, best illustrated by FIGS. 12-14, has an operational central axis that is the same as the elongate axis A' associated with the shank 204, but when the retainer structure 212 is separated from the shank 204, the axis of rotation is identified as axis C', as shown in FIG. 14. The retainer structure 212 has a central bore 282 that passes entirely through the retainer structure 212 from a top surface 284 to a bottom surface 285 thereof. A first inner cylindrical surface 286 defines a substantial portion of the bore 282, the surface 286 having a helically wound advancement structure thereon as shown by a helical rib or thread 288 extending from adjacent the top surface 284 to adjacent a seating surface 290 disposed perpendicular to the inner surface 286.

Although a simple helical rib 288 is shown in the drawings, it is foreseen that other helical structures including other types of threads, such as buttress and reverse angle threads, and non threads, such as helically wound flanges with interlocking surfaces, may be alternatively used in an alternative embodiment of the present embodiment. The first inner cylindrical surface 286 with helical rib 288 are configured to mate under rotation with the capture structure outer surface 238 and helical advancement structure or thread 240, as described more fully below.

The retainer structure 212 further includes a second inner cylindrical surface 292, coaxial with the first inner cylindrical surface 286. The surface 292 is disposed between the seating surface 290 and the bottom surface 285 of the retainer structure 212 and has a diameter greater than that of the cylindrical surface 286. As will be described more fully below, the cylindrical surface 292 in cooperation with the seating surface 290, provide a recess for insertion of the shank 204 thereinto and the seating surface 290 provides a frictional contact or seating surface for the seating surface 236 of the capture structure 108 as shown in FIGS. 18 and 19.

The retainer structure or ring 212 has a radially outer partially spherically shaped surface 294 sized and shaped to mate with the partial spherical shaped seating surface 272 of the head and having a third radius approximately equal to the first radius associated with the surface 272. The retainer structure third radius is larger than the second radius R' of the restrictive neck 274 of the head 210.

The retainer structure 212 shown in FIG. 13 further includes a transverse slot 296 formed in the top surface 284 thereof for engagement of the driving tool 231 shown in FIG. 22. It is foreseen that a retainer structure according to the present invention may include two or more slots in the retainer top surface, or other types of apertures for engaging with a cooperating driving tool. The slot 296 is defined by a pair of spaced, parallel walls 298 perpendicular to a base 300. The slot 296 extends out to the outer spherical surface 294 from each side of the central bore 282. A plane aligned with the center of the slot 296 intersects the rotational axis C'. The tool 231 includes a pair of spaced slot engaging extensions 302 sized and shaped to seat in the slot 296 on either side of the central bore 282 and with the region therebetween configured to clear the rod-engagement dome 242 during assembly and while driving and rotating the shank body 206 into the vertebra 215.

With reference to FIGS. 20 and 21, the slot 296 is preferably sized such that, after the shank 204, head 210 and retainer structure 12 have been assembled, a tool such as the illustrated punch 304 may be inserted into the slot 296 to deform the helical rib 240 of the capture structure 208 by causing a nick or deformity 305 thereon, thereby preventing relative rotation therebetween and rigidly fixing the rib 240 against the helical rib 288 of the retainer structure 212, ensuring a fixed relation between the shank capture structure 208 and the retainer structure 212.

The elongate rod or longitudinal member 221 that is utilized with the assembly 201 can be any of a variety of implants utilized in reconstructive spinal surgery, but is normally a cylindrical elongate structure having a cylindrical surface 306 of uniform diameter. The rod 221 is preferably sized and shaped to snugly seat at the lower channel seat 258 near the bottom of the U-shaped channel 256 of the head 210, and, during normal operation, is positioned slightly above the bottom of the channel 256. In particular, the rod 221 normally engages the shank top surface or dome 242, as shown in FIG. 24 and is biased against the dome 242, consequently biasing the shank 204 downwardly in a direction toward the base 250 of the head 210 when the assembly 201 is fully assembled.

With reference to FIGS. 23-25, the closure or top assembly 218 can be any of a variety of different types of closure structures for use in conjunction with the present invention with suitable mating structure internally or externally on the upstanding arms 252 and 254. The illustrated closure top assembly 218 includes a cylindrical closure plug 310 and a cylindrical inner set screw or plug 312. The inner plug 312 includes a pointed rod engaging projection or point 314 at a bottom surface thereof and a tool engagement aperture 315 disposed in an opposite or top surface thereof, illustrated in FIGS. 24 and 25 as a hex aperture. However, the tool engagement structure 315 may take a variety of tool-engaging forms and may include more than one aperture, such as a pair of spaced apertures or other shapes such as Torx or the like.

The closure plug 310 includes an outer helically wound guide and advancement structure 316 that is sized, shaped and positioned so as to engage the guide and advancement structure 262 on the arms 252 and 254 to provide for the rotation of the closure plug 310 into the head 210 and, in particular, to enclose the top of the U-shaped channel 56 to capture the rod 221, preferably without splaying of the arms 252 and 254. The closure plug 310 is a hollow cylinder and also includes an inner threaded cylindrical wall 317 sized and shaped to receive and rotatingly mate with an outer threaded surface 318 of the inner plug or set screw 312. As shown in FIG. 25, the closure plug 310 further includes a pair of transverse slots 319 in perpendicular relation, the slots 319 for engagement with a driving tool (not shown). The hex aperture 315, closure plug inner wall 317, inner plug wall 318, and arms 252 and 254 are configured so as to be coaxial upon assembly. A hex driving tool 320 can be inserted into the aperture 315 of the inner plug 312 to drive and rotate both the inner plug 312 into the closure plug 310 and the closure plug 310 into the head arms 252 and 254. Preferably, the closure plug 310 is first driven and rotated into the arms 252 and 254 by engaging a tool with the slots 319, followed by the inner plug 312 being rotated individually into the closure plug 312 by engagement with the tool 320.

The closure assembly 218 operably biases against the rod 221, with the projection 314 frictionally engaging and abrading the rod surface 306 and thereby applying pressure to the rod 221 under torquing, so that the rod 221 is urged downwardly against the rod-engagement dome 242. Downward biasing of the dome 242 operably produces a frictional engagement between the rod 221 and the dome 242 and also urges the retainer structure 212 toward the base 250 of the head 210, so as to frictionally seat the retainer structure external spherical surface 294 fixedly or in a locked configuration against the partial internal spherical seating surface 272 of the head 210, also fixing the shank 204 and retainer structure 212 in a selected, rigid angular position relative to the head 210.

If necessary, the hex tool 320 may be used to loosen the assembly subsequent to installation, and for removal of the plugs 310 and 312.

When the polyaxial bone screw assembly 201 is placed in use according to the invention, the closed ring-like retainer structure 212 is typically first inserted or top-loaded, into the head U-shaped channel 256 and then into the cavity 268 within the inner surface 270 of the head 210. Although not shown, the inner surface 270 may include a loading recess similar to the recess 87 disclosed with respect to the first embodiment assembly 1, and may be loaded into the head 210 in similar fashion. The retainer structure 212 is then seated with the surface 294 in sliding engagement with the spherical seating surface 272 of the head 210, as shown in FIG. 17. Although not required, both the retainer structure and head surfaces 294 and 272, respectively maybe high friction surfaces, such as knurled surfaces, or the like.

With reference to FIGS. 17 and 18, the shank capture structure 208 is inserted or bottom-loaded into the head 210 through the bore 276 defined by the neck 274. The retainer structure 212, now disposed in the head 210 is coaxially aligned with the shank capture structure 208 so that the helical advancement structure 240 of the capture structure 208 rotatingly mates with the helical advancement structure 288 of the retainer structure 212. The shank 204 and or the retainer structure 212 are rotated to fully mate the structures 240 and 288 along the respective cylindrical surfaces 238 and 286, as shown in FIG. 18, securing or fixing the capture structure 208 to the retainer structure 212, until the seating surface 236 and the seating surface 290 are in frictional contact, as shown in FIG. 19.

With reference to FIGS. 20 and 21, permanent, fixed or rigid engagement of the capture structure 208 to the retainer structure 212 may be further enhanced by deforming the helical advancement structure or thread 240 by inserting the pointed tool 304 into the slot 296 and marring or nicking the helical rib 240 with the tool 304, resulting in the nick or deformity 305, as is shown in FIG. 21. The deformity 305 causes the rib 240 to abut against the helical rib 288 of the retainer structure 212, thereby resisting unscrewing and ensuring a fixed relation between the shank capture structure 208 and the retainer structure 212. As with the assembly 1, the fixed relation between the rib 240 and the rib 288 may also be accomplished by the use of an adhesive, or spot weld or the like, in any area of the retainer structure cylindrical surface 238, especially where exposed by the slot 296.

As shown in FIG. 19, the shank 204 with integral capture structure 208 and attached retainer structure 212 are in pivotable engagement with the head 210. The capture structure 208 and the neck 274 of the head 210, connecting the shank 204 to the head 210 and after locking the retainer structure 212 keeping the shank body 206 in fixed rotational relation with the head 210.

According to the embodiment of the invention shown in FIGS. 12-25, only the retainer structure 212 is in slidable engagement with the head spherical seating surface 272. The capture structure 208 and threaded portion of the shank body 206 are in spaced relation with the head 210, although the shank outer neck 226 could engage the head restrictive neck 274 at a full rotation, as best illustrated in FIG. 24.

An extent of rotation is shown in FIG. 19 in phantom lines where it is illustrated that the shank body 206 can be rotated through a substantial angular rotation relative to the head 210, both from side to side and from front to rear so as to substantially provide a universal or ball joint wherein the angle of rotation is only restricted by engagement of the neck 226 of the shank body 206 with the neck 274 of the head 210.

With reference to FIG. 22, the assembly 201 is then typically screwed into a bone, such as the vertebra 215, by rotation of the shank 204 using the driving tool 231 that operably drives and rotates the shank 204 by engagement thereof with the transverse slot 296 of the retainer structure 212. Preferably, when the driving tool 231 engages the retainer structure 212, each of the tool prong like extensions 302 are disposed in a recess defined by the slot walls 298 and the base of the slot 300, with the tool extensions 302 seated upon and driving against the slot base 300.

The head 210 and the retainer structure 212 are assembled on the shank 204 before inserting the shank body 206 into the vertebra 215. With reference to FIG. 16 and FIG. 22, the vertebra 215 may be pre-drilled to minimize stressing the bone, as well as the connection between the retainer ring and capture structure, and a guide wire inserted to provide a guide for the placement and angle of the shank 204 with respect to the vertebra 215 (not shown). A bone screw shaped tap hole may be made utilizing a tap. Then, the assembly 201 or the solitary shank 204, is threaded onto the guide wire utilizing the cannulation bore 244 by first threading the wire into the bottom opening 246 and then out of the top opening 248. The shank 204 is then driven into the vertebra 215, using the wire as a screw placement guide and the wire is then removed.

With reference to FIGS. 23-25, the rod 221 is eventually positioned within the head U-shaped channel 256, and the closure assembly 218 is then inserted into and advanced between the arms 252 and 254 so as to bias or push against the rod 221. Specifically, a driving tool (not shown, but could be the same tool 231 shown in FIG. 22) is inserted into the slots 319 of the closure plug 310 to drive and rotate the closure plug 310 into the head arms 252 and 254. Subsequently, the hex driving tool 320 is inserted into the aperture 315 of the inner plug 312 to drive and rotate the inner plug 312 into the closure plug 310.

The shank top end surface or dome 242, because it is rounded and sized to extend upwardly into the U-shaped channel 256, is engaged by the rod 221 and pushed downwardly toward the base 250 of the head 210 when the outer closure structure and inner plug projection 314 bias downwardly toward and onto the rod 221. The downward pressure on the shank 204 in turn urges the retainer structure 212 downward toward the head seating surface 272, with the retainer structure seating surface 294 into frictional engagement with the head seating surface 272. As the outer plug and inner set screw 312 press against the rod 221, the rod 221 presses against the shank and rigidly attached retainer structure 212, which in turn becomes rigidly and frictionally attached to the head 210, fixing the shank body 206 in a desired angle with respect to the head 210 and rod 221.

FIGS. 24 and 25 illustrate the polyaxial bone screw assembly 201, the rod 221 and the closure assembly 218 positioned in the vertebra 215. The axis A' of the bone shank 204 is illustrated as not being coaxial with the axis B' of the head 210 and the shank 204 is fixed in this angular locked configuration. Other angular configurations can be achieved, as required during installation surgery due to positioning of the rod 221 or the like.

If removal of the assembly 201 and associated rod 221 and closure assembly 218 is necessary, disassembly is accomplished by using the driving tool 320 mating with the aperture 315 to rotate the inner plug or set screw 312 and reverse the advancement thereof in the outer closure plug 310. Subsequently, the outer plug 310 is loosened by mating the slots 319 with a driver (not shown) to reverse the advancement of the plug 310 in the arms 252 and 254. It may be possible to loosen both the inner plug 312 and the closure plug 310 with the tool 320, thus loosening the closure plug 310 from the head arms 252 and 254, as the outer plug 310 and inner plug 312 may be joined together by threads at the lower ends thereof becoming deformed by engagement with the rod 221. Then, disassembly of the assembly 1 is accomplished in reverse order to the procedure described previously herein for assembly. For disassembly, it is preferred that the retaining structure 312 be strongly secured to the shank 310 by deformation of the threads 238 and 288 or by other locking structure such as welding or pins so that both are assured of being removed as a single unit.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone screw assembly comprising:
   (a) a shank having a body for fixation to a bone and a capture structure extending upward from the body, the capture structure having an outer surface with a first helically wound guide and advancement structure, the shank extending above the capture structure so as to have an upper surface spaced from the capture structure;
   (b) a head having a top portion and a base, the head top portion defining an open channel sized and shaped to receive a rod, the base having a seating surface partially defining a cavity, the channel being located directly above and communicating with the cavity, the cavity communicating with an exterior of the base through an opening sized and shaped to receive the capture structure therethrough; and
   (c) a retainer structure having an external surface and a central bore with an internal surface having a second helically wound guide and advancement structure thereon, the first helically wound guide and advancement structure configured to rotatably mate with the second helically wound guide and advancement structure to secure the retainer structure to the capture structure within the head cavity, the external surface configured to be in slidable mating engagement with the seating surface of the head so as to enable selective angular positioning of the shank body with respect to the head, the retainer structure being positioned in spaced relationship from and beneath the shank upper surface and the shank upper surface adapted to receive locking pressure from a pressure structure located above the shank upper surface such that, between the shank upper surface and the retainer, only the shank upper surface engages the pressure structure.

2. The assembly of claim 1 wherein:
   (a) the head seating surface that is located to be in slidable mating engagement with the retainer structure external surface is substantially partially spherical; and
   (b) the retainer structure external surface that is in slidable mating engagement with the head seating surface is substantially partially spherical.

3. The assembly of claim 1 wherein the capture structure has a tool engagement formation disposed thereon adapted for non-slip engagement by a tool for driving the shank body into bone.

4. The assembly of claim 3 wherein the capture structure tool engagement formation is an axial projection having a hexagonal profile.

5. The assembly of claim 3 wherein the tool engagement formation is a projection and the retainer structure has a tool seating surface, the projection and the tool seating surface partially defining a recess for receiving a driving tool engaged with the tool engagement projection and wherein the driving tool is adapted to be in contact with the tool seating surface when driving the shank body into bone.

6. The assembly of claim 3 wherein the tool engagement formation is a projection and the capture structure has a tool seating surface, the projection and the tool seating surface partially defining a recess about a base of the projection adapted for receiving a driving tool engaged with the tool engagement projection and wherein the driving tool is adapted to be in contact with the tool seating surface when driving the shank body into bone.

7. The assembly of claim 3 wherein the tool engagement formation is a projection, the retainer structure has a first seating surface, and the capture structure has a second seating surface; the projection, the first seating surface and the second seating surface partially defining a recess at a base of the projection adapted for receiving a driving tool engaged with the tool engagement projection and wherein the driving tool is adapted to be in contact with both the first and second seating surfaces when driving the shank body into bone.

8. The assembly of claim 1 wherein the first helically wound guide and advancement structure is a raised helical rib.

9. The assembly of claim 1 wherein the second helically wound guide and advancement structure is a raised helical rib.

10. The assembly of claim 1 wherein the shank is cannulated.

11. The assembly of claim 1 wherein the retainer structure has a first planar seating surface and the capture structure has a second planar seating surface, the first and second planar seating surfaces being in contact when the retainer structure is secured to the capture structure.

12. The assembly of claim 11 wherein the retainer structure has a second internal surface, the second internal surface and the first planar seating surface partially defining a recess, the second planar seating surface disposed in the recess when the retainer structure is secured to the capture structure.

13. The assembly of claim 1 wherein the retainer structure is sized and shaped to be loadable into the head through the open channel and the shank is sized and shape to be loadable into the head through the base opening.

14. The assembly of claim 13 wherein the head seating surface includes a recess shaped and sized for providing for and guiding the insertion of the retainer structure into the cavity.

15. The assembly of claim 1 further comprising a closure structure insertable into the head, the closure structure for operably urging the shank in a direction to frictionally lock the position of the retainer structure external surface relative to the head seating surface, thereby locking the shank body in a selected angle with respect to the head.

16. The assembly of claim 15 wherein:
(a) the head has upstanding spaced arms defining the open channel, the arms having guide and advancement structures on an inside surface thereof; and
(b) the closure structure is sized and shaped to be positionable between the arms for closing the channel, the closure structure having a closure guide and advancement structure for rotatably mating with the guide and advancement structures on the arms, biasing the closure structure upon advancement rotation against a rod disposed in the channel.

17. The assembly according to claim 1 including a pressure structure and wherein the pressure structure is a rod received in the head channel.

18. The assembly according to claim 1 wherein:
(a) the shank includes an external driving surface located between the shank upper surface and the retainer after the assembly is assembled.

19. In a polyaxial bone screw assembly for surgical implantation and including a shank having an upper end and a threaded body for inserting into a bone and a head having an outward opening channel adapted to receive a rod within the channel, the head having a shank receiving opening, the improvement comprising:
(a) a capture structure disposed on the shank upper end sized and configured to be uploaded through the shank receiving opening, the capture structure having an outer surface with a first helically wound advancement structure; and
(b) a closed retainer structure having an external surface and an internal surface with a second helically wound advancement structure, the first helically wound advancement structure configured to rotatably mate with the second helically wound advancement structure to secure the retainer structure to the capture structure within the head, when assembled and in a non-locked configuration, the retainer structure and the shank being polyaxially rotatable together relative to the head and the retainer structure external surface enabling selective angular positioning of the shank with respect to the head during polyaxial rotation, the shank capture structure extending above the retainer after assembly so as to provide an engagement top surface of the shank spaced from and above the retainer, the engagement top surface being sized, shaped and positioned to receive a downward force from a rod received in the head so as to frictionally lock the shank in a fixed angular position relative to the head in a locked configuration.

20. The improvement of claim 19 wherein:
(a) the head has an inner substantially spherical seating surface partially defining a cavity, the cavity being positioned below and communicating with both the channel and the shank receiving opening;
(b) a rod positioned in the channel when the assembly is assembled;
(c) the retainer structure external surface is partially spherical in shape and in slidable mating engagement with the head seating surface; and
(d) the shank upper end extends into the channel when the bone screw assembly is fully assembled and is positioned to directly engage the rod when received in the channel and thereby receive a downward locking force directly from the rod in the channel.

21. The improvement of claim 19 wherein the capture structure has a tool engagement formation disposed thereon for non-slip engagement by a tool for driving the shank body into bone.

22. The improvement of claim 21 wherein the tool engagement formation is a projection and the retainer structure has a tool seating surface, the projection and the tool seating surface partially defining a recess for receiving a driving tool engaged with the tool engagement projection and wherein the driving tool is adapted to be in contact with the tool seating surface when driving the shank body into bone.

23. The improvement of claim 21 wherein the tool engagement formation is a projection and the capture structure has a tool seating surface, the projection and the tool seating surface partially defining a recess about a base of the projection adapted for receiving a driving tool engaged with the tool engagement projection and wherein the driving tool is adapted to be in contact with the tool seating surface when driving the shank body into bone.

24. The improvement of claim 21 wherein the tool engagement formation is a projection, the retainer structure has a first seating surface, and the capture structure has a second seating surface; the projection, the first seating surface and the second seating surface partially defining a recess adapted for receiving a driving tool engaged with the tool engagement projection and wherein the driving tool is adapted to be in contact with both the first and second seating surfaces when driving the shank body into bone.

25. The improvement of claim 19 wherein the first helically wound advancement structure is a raised helical rib.

26. The improvement of claim 25 wherein the second helically wound advancement structure is a raised helical rib.

27. The improvement of claim 19 wherein the retainer structure has a first planar seating surface and the capture structure has a second planar seating surface, the first and second planar seating surfaces being in contact when the retainer structure is secured to the capture structure.

28. A polyaxial bone screw assembly comprising:
(a) a shank having a threaded body for fixation to a bone and a capture structure extending from the body, the capture structure having an outer substantially cylindrical surface with a first raised helical rib disposed thereon;
(b) a head having a top portion and a base, the top portion defining an open channel, the base having a partial substantially spherical seating surface partially defining a cavity, the channel being located above and communicating with the cavity, the cavity communicating with an exterior of the base through an opening therein sized and shaped to receive the capture structure therethrough;
(c) a closed retainer structure having an external partial spherical surface and an internal substantially cylindrical surface having a second raised helical rib disposed thereon, the first rib configured to rotatably mate with the second rib to secure the retainer structure to the capture structure within the head cavity with the external surface oriented in slidable mating engagement with the seating surface of the head when in a non locked configuration; and
(d) a tool engagement formation disposed on the capture structure and extending above the retaining structure, the formation adopted for non-slip engagement by a tool for driving the shank body into bone.

29. The assembly of claim 21 wherein the tool engagement formation is a projection extending axially from the capture structure, the projection partially defining a recess about a base of the projection adapted for receiving a driving tool engaged with the tool engagement projection and wherein the driving tool is adapted to be in contact with the tool seating surface when driving the shank body into bone.

30. The assembly of claim 28 wherein the tool engagement formation is a projection extending axially from the capture structure and the capture structure has a tool seating surface, the projection and the tool seating surface partially defining a recess about a base of the projection adapted for receiving a driving tool engaged with the tool engagement projection and wherein the driving tool is adapted to be in contact with the tool seating surface when driving the shank body into bone.

31. The assembly of claim 28 wherein the retainer structure has a first planar seating surface and the capture structure has a second planar seating surface, the first and second planar seating surfaces being in contact when the retainer structure is secured to the capture structure.

32. The assembly of claim 31 wherein the retainer structure has a second internal surface, the second internal surface and the first planar seating surface partially defining a recess, the second planar seating surface being disposed in the recess when the retainer structure is secured to the capture structure.

33. The assembly of claim 28 wherein the retainer structure is sized and shaped to be loadable into the head through the open channel and the shank is sized and shape to be loadable into the head through the base opening.

34. The assembly of claim 33 wherein the head seating surface defines a recess shaped and sized for facilitating the insertion of the retainer structure into the cavity.

35. The assembly of claim 28 further comprising a closure structure insertable into the head, the closure structure closing a top of the channel and adapted to operably urge the shank in a direction to frictionally fix the retainer external surface to the head seating surface, thereby rigidly positioning the shank body in a selected angle with respect to the head.

36. The assembly of claim 35 wherein:
(a) the head has upstanding spaced arms defining the open channel, each of the arms having guide and advancement structures on an inside surface thereof; and
(b) the closure structure is disposable between the arms for closing the channel, the closure structure having an advancement structure for rotatably mating with the guide and advancement structures on the arms, thereby biasing the closure structure against a rod disposed in the channel when rotated in an advancement direction.

37. In a polyaxial bone screw having a shank and a head with an internal cavity and a receiving bore connecting the cavity with an underside of the head and a rod receiving channel communicating with the cavity; the improvement comprising wherein:
(a) the shank has an upper threaded capture structure with an upper engagement surface, the head channel being located over the shank upper engagement surface when the bone screw is assembled; and including;
(b) a ring-like retainer structure that is operably received in the cavity and has a closed threaded bore; and
(c) the threaded capture structure being threadedly received in the retainer structure threaded bore to secure the shank to the head with the upper engagement surface spaced from and above the retainer structure.

38. A polyaxial bone screw assembly comprising:
(a) a shank having a body for fixation to a bone and a capture structure extending from the body, the capture structure having an outer surface with a first helically wound guide and advancement structure;
(b) a head having a top portion and a base, the head top portion defining an open channel, the base having a seating surface partially defining a cavity, the channel being located above and communicating with the cavity, the cavity communicating with an exterior of the base through an opening sized and shaped to receive the capture structure therethrough; and
(c) a closed retainer structure having an external surface and a central bore with an internal surface having a second helically wound guide and advancement structure thereon, the first helically wound guide and advancement structure configured to rotatably mate with the second helically wound guide and advancement structure to secure the retainer structure to the capture structure within the head cavity, the external surface being continuous and uniform, the external surface being configured to be in slidable mating engagement with the seating surface of the head so as to enable selective angular positioning of the shank body with respect to the head.

39. A polyaxial bone screw assembly comprising:
(a) a shank having a body for fixation to a bone and a capture structure extending from the body, the capture structure having an outer surface with a first helically wound guide and advancement structure;
(b) a head having a top portion and a base, the head top portion having a pair of spaced upstanding arms defining an open channel with a width between the arms, the base having a seating surface partially defining a cavity, the channel communicating with the cavity, the cavity communicating with an exterior of the base through an opening sized and shaped to receive the capture structure therethrough; and (c) a retainer structure having an external surface and a central bore with an internal surface having a second helically wound guide and advancement structure thereon, the retainer structure having a height less than the channel width such that during loading of the retainer into the head cavity, the retainer can be turned sideways so as to pass through the channel into the cavity, the first helically wound guide and advancement structure configured to rotatably mate with the second helically wound guide and advancement structure to secure the retainer structure to the capture structure within the head cavity, the external surface configured to be in slidable mating engagement with the seating surface of the head so as to enable selective angular positioning of the shank body with respect to the head.

40. A polyaxial bone screw assembly comprising:

(a) a shank having a body for fixation to a bone and a capture structure extending upward from the body, the capture structure having an outer surface with a first helically wound guide and advancement structure, the shank extending above the capture structure so as to have a shank upper surface above the capture structure;

(b) a head having a top portion and a base, the head top portion defining an open channel sized and shaped to receive an elongated member, the base having a seating surface partially defining a cavity, the channel being located directly above and communicating with the cavity, the cavity communicating with an exterior of the base through an opening sized and shaped to receive the shank capture structure therethrough; and (c) a retainer structure having an external surface and a central bore with an internal surface having a second helically wound guide and advancement structure thereon, the first helically wound guide and advancement structure configured to rotatably mate with the second helically wound guide and advancement structure to secure the retainer structure to the shank capture structure within the head cavity, the external surface configured to be in slidable mating engagement with the seating surface of the head so as to enable selective angular positioning of the shank body and secured retainer with respect to the head, the retainer structure being positioned in spaced relationship from and beneath the shank upper surface and the shank upper surface adapted to receive locking pressure from a pressure structure located above the shank upper surface such that, between the shank upper surface and the retainer, only the shank upper surface engages the pressure structure.

41. A polyaxial bone screw assembly comprising:

(a) a shank having a body for fixation to a bone and a capture structure extending upward from the body, the capture structure having an outer surface with a first helically wound guide and advancement structure, the shank extending above the capture structure so as to have a shank upper surface above the capture structure;

(b) a head having a top portion and a base, the head top portion defining an open channel and a central bore sized and shaped to receive a pressure-bearing structure, the base having a seating surface partially defining a cavity, the channel being located directly above and communicating with the cavity, the cavity communicating with an exterior of the base through an opening sized and shaped to receive the capture structure therethrough; and (c) a retainer structure having an external surface and a central bore with an internal surface having a second helically wound guide and advancement structure thereon, the first helically wound guide and advancement structure configured to rotatably mate with the second helically wound guide and advancement structure to secure the retainer structure to the shank capture structure within the head cavity, the external surface configured to be in slidable mating engagement with the seating surface of the head so as to enable selective angular positioning of the shank body and secured retainer with respect to the head, the retainer structure being positioned in spaced relationship from and beneath the shank upper surface and the shank upper surface adapted to receive locking pressure from said pressure-bearing structure located above the shank upper surface such that, between the shank upper surface and the retainer, only the shank upper surface engages the pressure-bearing structure.

* * * * *